United States Patent
Blumenkranz

(10) Patent No.: US 12,048,817 B2
(45) Date of Patent: Jul. 30, 2024

(54) BACKEND MECHANISM OF A CATHETER CONTROL SYSTEM

(71) Applicant: INTUITIVE SURGICAL OPERATIONS, INC., Sunnyvale, CA (US)

(72) Inventor: Stephen J. Blumenkranz, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 859 days.

(21) Appl. No.: 17/047,414

(22) PCT Filed: May 10, 2019

(86) PCT No.: PCT/US2019/031823
§ 371 (c)(1),
(2) Date: Oct. 14, 2020

(87) PCT Pub. No.: WO2019/222058
PCT Pub. Date: Nov. 21, 2019

(65) Prior Publication Data
US 2021/0138195 A1    May 13, 2021

Related U.S. Application Data

(60) Provisional application No. 62/671,958, filed on May 15, 2018.

(51) Int. Cl.
*A61M 25/01*   (2006.01)
*A61B 34/00*   (2016.01)
(Continued)

(52) U.S. Cl.
CPC ......... *A61M 25/0113* (2013.01); *A61B 34/71* (2016.02); *A61B 34/35* (2016.02);
(Continued)

(58) Field of Classification Search
CPC .......... A61M 25/0113; A61M 25/0147; A61B 34/71; A61B 2034/715; A61B 2034/301
See application file for complete search history.

(56) References Cited

U.S. PATENT DOCUMENTS 6,380,732 B1   4/2002   Gilboa
6,389,187 B1   5/2002   Greenaway et al.
(Continued)

FOREIGN PATENT DOCUMENTS

JP    2007527296 A    9/2007
WO   WO-2010009224 A1   1/2010
(Continued)

OTHER PUBLICATIONS

International Search Report and Written Opinion for Application No. PCT/US2019/031823, dated Oct. 29, 2019, 18 pages (ISRG11520/PCT).

(Continued)

*Primary Examiner* — Bradley J Osinski
(74) *Attorney, Agent, or Firm* — Haynes & Boone, LLP.

(57) ABSTRACT

A control system for an elongate member actuated via a pull wire comprises a chassis fixable in place relative to the elongate member during use and a pulley carried by the chassis, the pulley having a first pull wire-supporting surface structurally configured to support the pull wire, the pulley being rotatable about a first axis. The system further comprises a wall carried by the chassis and a capstan carried by the chassis and rotatable about a second axis aligned at an orthogonal angle relative to the first axis, the capstan having a second pull wire-supporting surface that permits the pull wire to wrap around the capstan, wherein the wall extends circumferentially around the capstan and includes a slit through which the pull wire extends.

20 Claims, 17 Drawing Sheets

(51) Int. Cl.
    *A61B 34/35* (2016.01)
    *A61B 34/37* (2016.01)
(52) U.S. Cl.
    CPC ......... *A61B 34/37* (2016.02); *A61B 2034/715* (2016.02); *A61M 2025/0166* (2013.01); *A61M 2205/3306* (2013.01)

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,138,166 | B2 | 9/2015 | Wong et al. |
| 9,259,274 | B2 | 2/2016 | Prisco |
| 9,452,276 | B2 | 9/2016 | Duindam et al. |
| 9,737,373 | B2 | 8/2017 | Schuh |
| 10,729,886 | B2 | 8/2020 | Fenech et al. |
| 2006/0013523 | A1 | 1/2006 | Childlers et al. |
| 2006/0084945 | A1 | 4/2006 | Moll et al. |
| 2011/0319815 | A1 | 12/2011 | Roelle et al. |
| 2014/0257333 | A1* | 9/2014 | Blumenkranz ........ A61B 34/71 606/130 |

FOREIGN PATENT DOCUMENTS

| | | |
|---|---|---|
| WO | WO-2014138365 A1 | 9/2014 |
| WO | WO-2017044874 A1 | 3/2017 |
| WO | WO-2017156070 A1 | 9/2017 |
| WO | WO-2018013313 A1 | 1/2018 |

OTHER PUBLICATIONS

Invitation to Pay Additional Fees dated Aug. 20, 2019 for PCT Application No. PCT/US2019/031823 filed on May 10, 2019, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2019/031823, dated Nov. 26, 2020, 10 pages.
Office Action for Chinese Application No. 201980033894.5, dated Nov. 10, 2023, 15 pages.

* cited by examiner

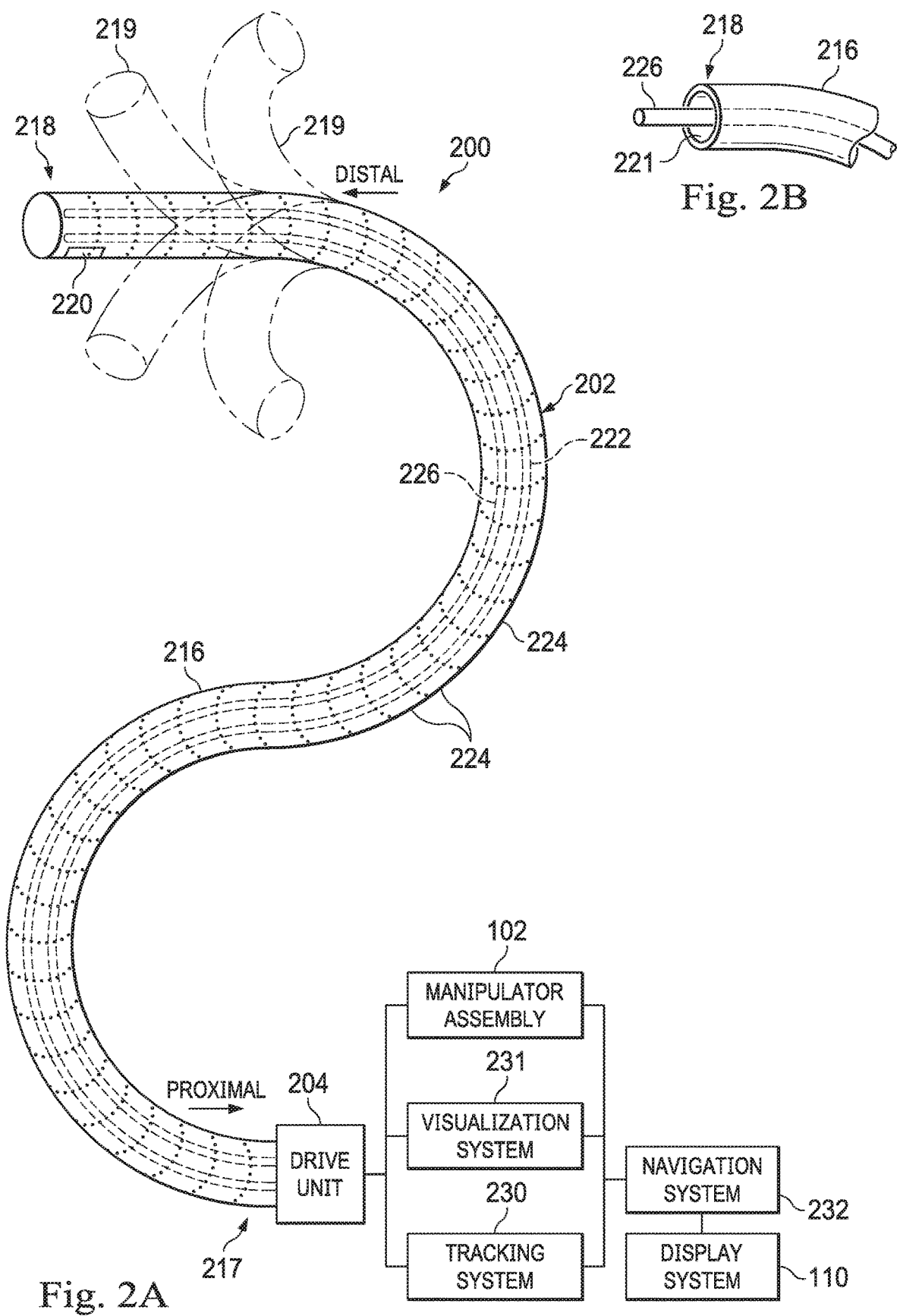

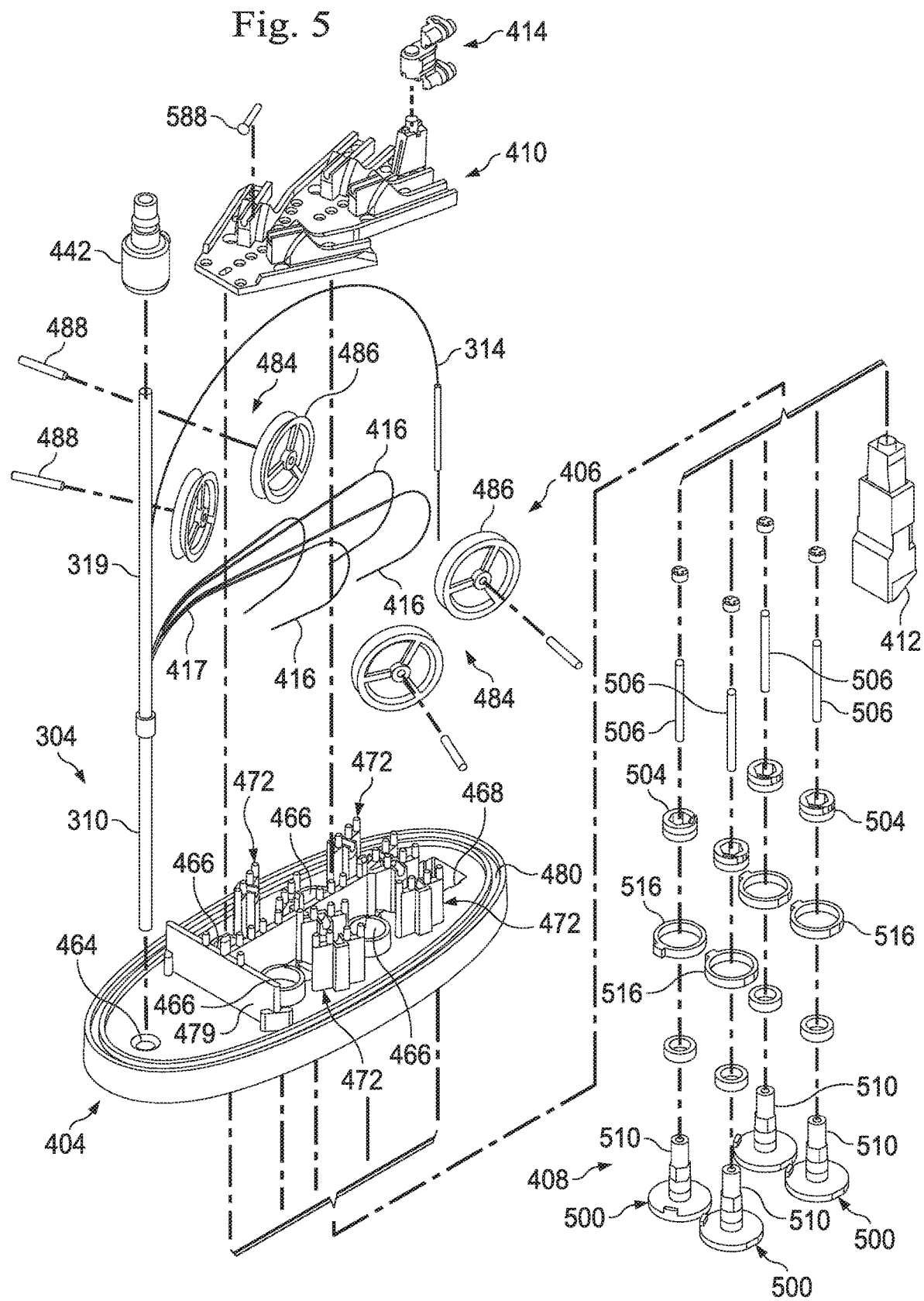

BACKEND MECHANISM OF A CATHETER CONTROL SYSTEM

CROSS-REFERENCE TO RELATED APPLICATIONS

This application is the U.S. national phase of International Application No. PCT/US2019/031823, filed May 10, 2019, which designated the U.S. and claims priority to and the benefit of U.S. Provisional Application No. 62/671,958 filed May 15, 2018, both of which are incorporated by reference herein in their entirety.

TECHNICAL FIELD

The present disclosure is directed to systems utilized in medical procedures and operational methods used during those procedures. More particularly, the present disclosure is directed to backend mechanisms of catheter control systems and related methods.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Backend mechanism control systems include components that enable steering or manipulation of the elongate device or instruments extending therethrough. The backend mechanism control system then cooperates with the elongate device to carry out the surgical technique under the control of a health care provider. To increase the likelihood of a successful surgical outcome, it would be desirable to provide a backend mechanism control system that is stable when in use, compact, and removable for sterilization. Furthermore, it would be desirable for the components of the backend mechanism control system that control the elongate device to provide a predictable and repeatable action for a consistent result under the control of the surgeon. In addition, it would be advantageous to provide a backend mechanism control system that provides control of steerable elongate devices, such as steerable catheters, that may be suitable for use during minimally invasive medical techniques.

SUMMARY

In general, the present disclosure is directed to systems and methods for steering an elongate member using a backend mechanism that cooperates with pull wires to actuatably steer via motors. Additional certain embodiments of the invention are best summarized by the claims that follow the description.

In some exemplary implementations, the present disclosure is directed to a control system for an elongate member steerable via a pull wire. The control system may include a chassis fixable in place relative to the elongate member during use and a pulley carried by the chassis. The pulley may include a pull wire-supporting surface structurally configured to support the pull wire. The pulley may be rotatable about a first axis. The control system also may include a capstan carried by the chassis and rotatable about a second axis aligned at an angle relative to the first axis. The capstan may have a pull wire-supporting surface that permits the pull wire to wrap around the capstan.

In some aspects, the chassis comprises a pocket having an opening therethrough through which the pull wire extends. In some aspects, the control system includes an input disk configured to drivably rotate the capstan. The input disk may include a shaft having non-cylindrical shape, and the capstan may be configured to interface with the non-cylindrical shape in a manner allowing the shaft to rotate the capstan. In some aspects, the capstan may include a helical groove arranged to wind the pull wire without overlap. In some aspects, the control system may include a rotation limiter arranged to prevent rotation of the capstan beyond a threshold position. In some aspects, the rotation limiter may include a mechanical stop arranged to prevent rotation of the capstan beyond the threshold position.

In some aspects, the control system may include a fiber optic connector extending from the chassis, and may include a shape sensing optical fiber extending from the fiber optic connector through a length of the elongate member. The shape sensor may be arranged to detect a shape of the elongate member. The fiber optic connector may be configured to communicate information detected by the shape sensor. In some aspects, the control system includes an enclosed housing that comprises a service loop adjacent a wall of the housing. The housing may include an arcing surface sized to accommodate bending of a shape sensor extending between a launch region fixture in the housing to the elongate member. In some aspects, the service loop is a 180 degree bend in the shape sensor. In some aspects, the housing comprises a guide defining a guide slot in which the shape sensor extends. In some aspects, the chassis comprises an elongate member opening defining a third axis disposed substantially parallel to the second axis. In some aspects, the control system includes a coil pipe having a proximal end fixed to the chassis at a connection location. The proximal end of the coil pipe may be disposed substantially orthogonal to the third axis defined by the elongate member opening, and the pull wire may extend through the coil pipe and to the pulley and thereby to the capstan. In some aspects, the chassis comprises a mounting face shaped and configured to interface with an instrument carriage arranged to drive the capstan. The mounting face may generally extend along a mounting plane and the mounting face may have a first interfacing portion and a second non-interfacing portion arranged side-by-side. The first interfacing portion may have a fiber connector and rotational input members. The second non-interfacing portion may have a first elongate member opening formed such that the elongate member extends from the elongate member opening in a direction substantially orthogonal to the mounting plane. In some aspects, the chassis comprises a mounting face having one of a plurality of v-shaped grooves and a plurality of locating mounts and the instrument carriage comprising the other of the plurality of v-shaped grooves and the plurality of locating mounts. The plurality of v-shaped grooves may be configured to receive the plurality of locating mounts.

In some aspects, the control system includes a cover attached to the chassis at an interface to form a cavity therein, the pulley being disposed in the cavity. An input disk may pass through an opening in the chassis and may be arranged to rotatably drive the capstan. The input disk having a shielding face to prevent ingress of fluids.

In another exemplary aspect, the present disclosure is directed to a control system for the elongate member that includes a housing comprising a plurality of steering components for steering the elongate member. The housing may have a mounting face shaped and configured to interface with an instrument carriage arranged to provide input to the steering components. The mounting face may extend generally along a mounting plane, with the mounting face having a first interfacing portion and a second non-interfacing portion arranged side-by-side. The first interfacing portion may have a fiber connector and rotational input members, and the second non-interfacing portion may have a first elongate member opening formed such that an elongate member in the elongate member opening extends in a direction substantially orthogonal to the mounting plane.

Some aspects include a kinematic mount arranged to selectively connect the housing to the instrument carriage in a uniquely determined position and orientation. In some aspects, the control system may include a kinematic mount arranged to selectively position and orient the housing to the instrument carriage. In some aspects, the housing comprises a plurality of latch connectors configured to selectively secure the housing to the instrument carriage. In some aspects, each of the rotational input members on the mounting face comprises an input disk mountable to and driven by an output disk on the instrument carriage, the input disk being in communication with the steering components. In some aspects, the mounting face comprises one of a printed circuit assembly and pogo pins and the instrument carriage comprises the other of the printed circuit assembly and the pogo pins, the circuit assembly being configured to communicate with pogo pins.

In yet other exemplary aspects, the present disclosure is directed to a control system for steering an elongate member that includes a housing comprising a chassis and a cover sealed together at an interface to form a cavity therein, a plurality of steering components for steering the elongate member being disposed in the cavity, with the interface being sealed to prevent ingress of fluids. A plurality of input disks may pass through openings in the chassis and arranged to rotatably drive the steering components, the input disks being shielded or sealed to prevent ingress of fluids or protected by a sealing cover to prevent ingress of fluids or protected by a sealing cover to prevent ingress of fluids.

In some aspects, the present disclosure includes a connector for attaching the housing to an instrument carriage, the connector comprising a shield or seal that prevents the ingress of fluid. In some aspects, the chassis comprises a peripheral groove, the cover having an edge sealingly fit into the peripheral groove. In some implementations, the sealing is accomplished through welding.

In yet other exemplary implementations, the present disclosure is directed to a control system for steering an elongate member that includes a chassis comprising a steering component support face and an opposing mounting face. The steering component support face may support a capstan operably coupled to a pull wire arranged to steer the elongate member. An input disk may be disposed at the mounting face and arranged to rotate the capstan to displace the pull wire. An optical fiber connector may be disposed on the mounting face and extending from the mounting face in a direction away from the steering component support face, the input disk and the optical fiber connector being disposed to engage an instrument carriage by translation of the chassis to attach the chassis to the instrument carriage.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 2A is a simplified diagram of a medical instrument system according to some embodiments.

FIG. 2B is a simplified diagram of a medical instrument with an extended medical tool according to some embodiments.

FIG. 5 is a diagram of a backend mechanism of a portion of a medical instrument in a partially exploded configuration according to some embodiments.

Figure 1:
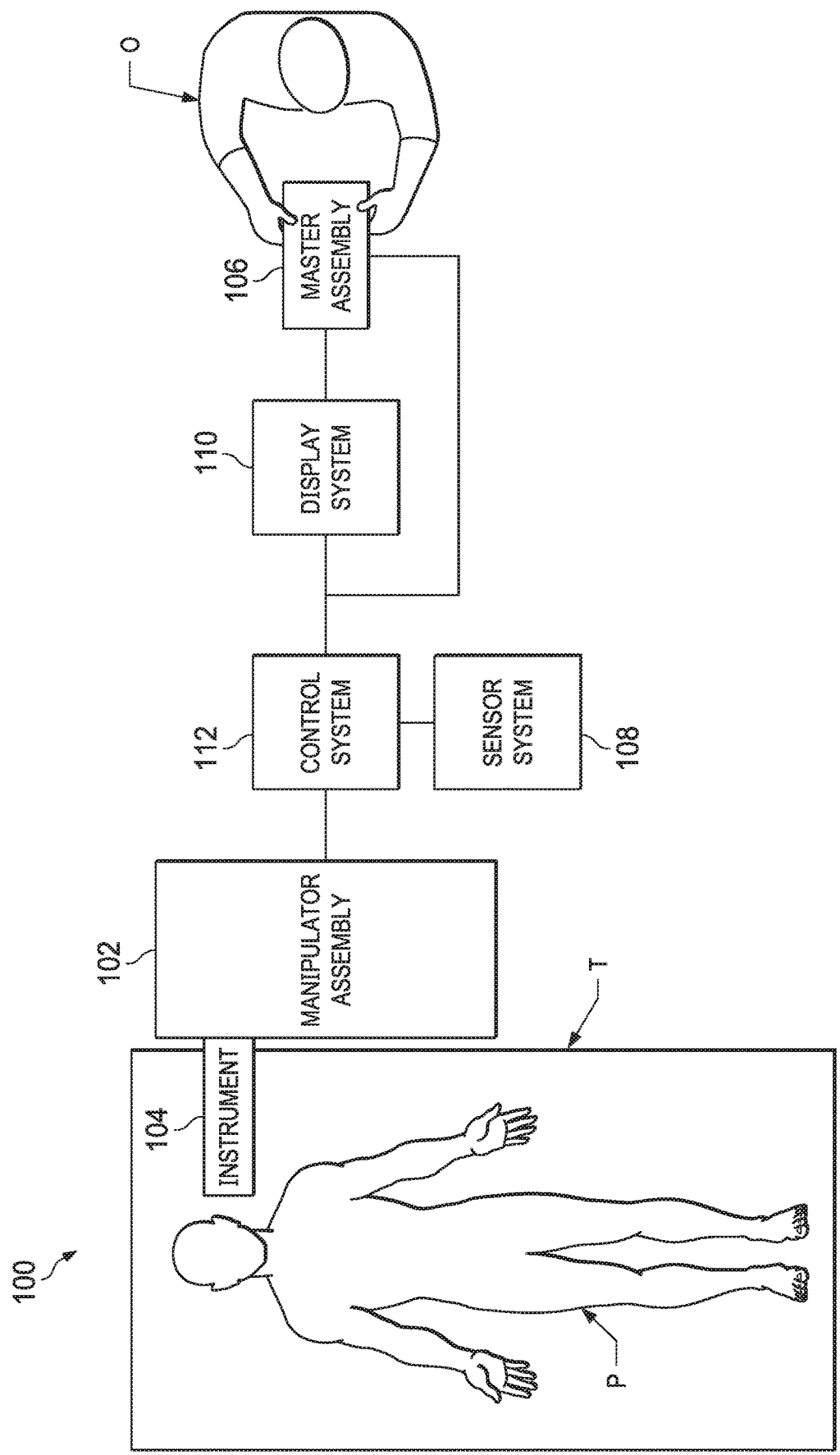
FIG. 1 is a simplified diagram of a teleoperated medical system adjacent a patient according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

For the purposes of promoting an understanding of the principles of the present disclosure, reference will now be made to the embodiments illustrated in the drawings, and specific language will be used to describe the same. In the following detailed description, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded preoperatively or intraoperatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate member 202, such as a flexible catheter, coupled to a drive unit 204. In some embodiments, drive unit 204 may be coupled to or integrated within manipulator assembly 102. Elongate member 202 includes a flexible body 216 having proximal end 217 and distal end 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel or lumen (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate member may be determined using other techniques.

For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate member 202, particularly if an anatomic passageway is generally static.

Flexible body 216 includes a channel 221 (FIG. 2B) sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, needle drivers, retractors, stabilizers and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties. In some embodiments, medical instrument 226 may include end effectors such as those previously described above which fixed to a distal end portion of medical instrument 226 or fixed to an articulatable wrist integrated into the distal end portion of medical instrument 226. Cables, linkages, or other actuation controls may be used to control actuation of the end effector (e.g. grasping, pinching, and/or cutting actuation) or control positioning of the end effector via the articulatable wrist. Such cables, linkages, or other actuation controls may terminate in and be controlled by mechanisms within a drive unit, such as drive unit 204.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable elongate members are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate member 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
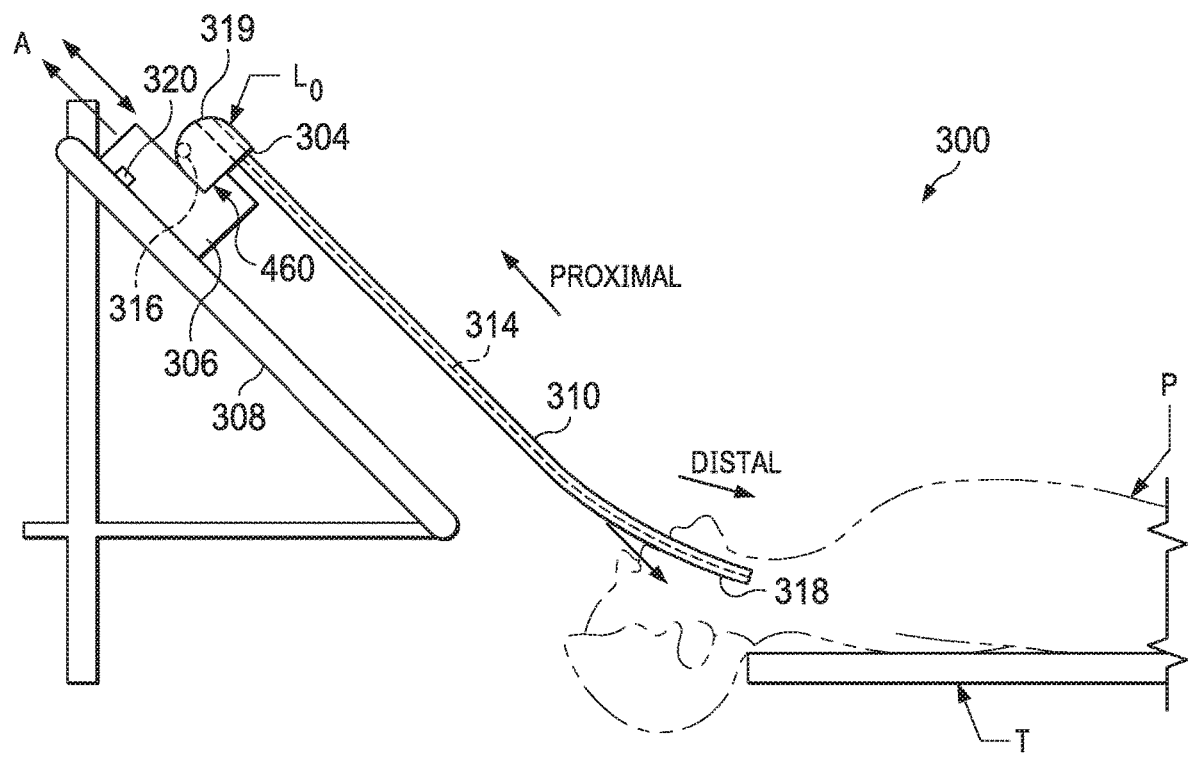
FIGS. 3A and 3B are simplified diagrams of side views of a medical instrument mounted on an insertion assembly and positioned to treat a patient according to some embodiments.
Figure 3B:
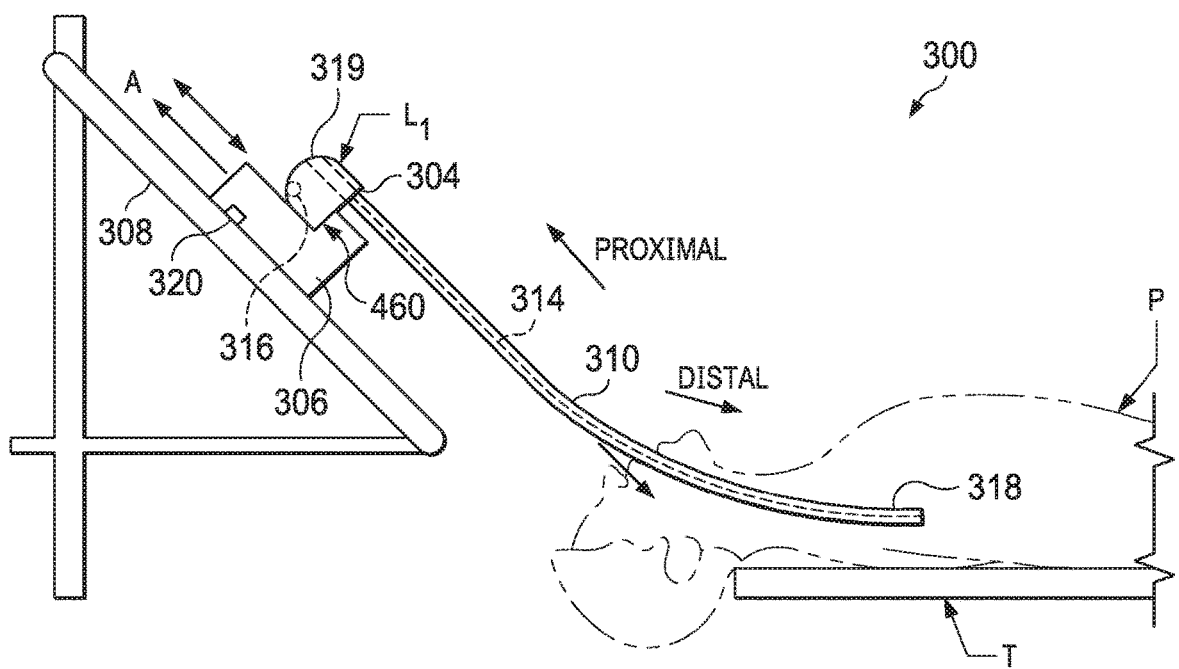

FIGS. 3A and 3B are simplified diagrams of side views of a medical instrument mounted on an insertion assembly and position to treat a patient according to some embodiments. As shown in FIGS. 3A and 3B, a surgical environment 300 includes a patient P positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a backend mechanism 304 can be removably coupled to an instrument carriage 306. In some embodiments, the backend mechanism 304 may be formed of a housing containing operational components for cables used to provide independent up down steering to control a pitch of distal end 318 and left right steering to control a yaw of distal end 318. In addition, the backend mechanism 304 may comprise EM sensors, shape-sensors, and/or other sensor modalities and or provide connectors coupling sensing modalities to an instrument such as elongate member 310.

Instrument carriage 306 can be mounted to an insertion stage 308 which is fixed within surgical environment 300. Alternatively, insertion stage 308 may be movable but have a known location (e.g., via a tracking sensor or other tracking device) within surgical environment 300. Instrument carriage 306 may be a component of a teleoperational manipulator or a non-teleoperational manipulator assembly (e.g., manipulator assembly 102) that controls insertion motion (i.e., motion along the A axis) and, optionally, motion of a distal end 318 of an elongate member 310 in multiple directions including yaw, pitch, and roll. Instrument carriage 306 or insertion stage 308 may include actuators, such as servomotors, (not shown) that control motion of instrument carriage 306 along insertion stage 308, control motion of the distal end 318 of elongate member 310 in yaw/pitch, and/or control roll motion of elongate member 310 along a longitudinal axis.

Elongate member 310 is coupled to backend mechanism 304. Backend mechanism 304 is coupled and fixed relative to instrument carriage 306. In some embodiments, an optical fiber shape sensor 314 is fixed at a proximal point 316 on backend mechanism 304. In some embodiments, proximal point 316 of optical fiber shape sensor 314 may be movable along with backend mechanism 304 but the location of proximal point 316 may be known (e.g., via a tracking sensor or other tracking device). Shape sensor 314 measures a shape from proximal point 316 to another point such as distal end 318 or a point along a distal portion of elongate member 310.

A position measuring device 320 provides information about the position of backend mechanism 304 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of backend mechanism 304. In some embodiments, insertion stage 308 is linear. In some embodiments, insertion stage 308 may be curved or have a combination of curved and linear sections.

FIG. 3A shows backend mechanism 304 and instrument carriage 306 in a retracted position along insertion stage 308. In this retracted position, proximal point 316 is at a position Lo on axis A. In this position along insertion stage 308 a component of the location of proximal point 316 may be set to a zero and/or another reference value to provide a base reference to describe the position of instrument carriage 306, and thus proximal point 316, on insertion stage 308. With this retracted position of backend mechanism 304 and instrument carriage 306, distal end 318 of elongate member 310 may be positioned proximal to, e.g. just inside, just outside, or otherwise near an entry orifice of patient P. Also in this position, position measuring device 320 may be set to a zero and/or another reference value (e.g., I=0). In FIG. 3B, backend mechanism 304 and instrument carriage 306 have advanced along the linear track of insertion stage 308 and distal end 318 of elongate member 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position Lo. In some examples, position $L_x$ may further be used as an indicator of the distance or insertion depth to which distal end 318 of elongate member 310 is inserted into the passageways of the anatomy of patient P.

In FIG. 3A, the backend mechanism 304 includes a mounting face 460, that may define a mounting plane. A portion of the mounting face 460, referred to as an interfacing region, is disposed against the instrument carriage 306, while another portion of the mounting face 460, referred to as a non-interfacing region, protrudes outwardly beyond an edge of the instrument carriage 306. As can be seen, the elongate member 310 extends from the backend mechanism 304, out of the mounting face 460, and past the instrument carriage 306.

Figure 4:
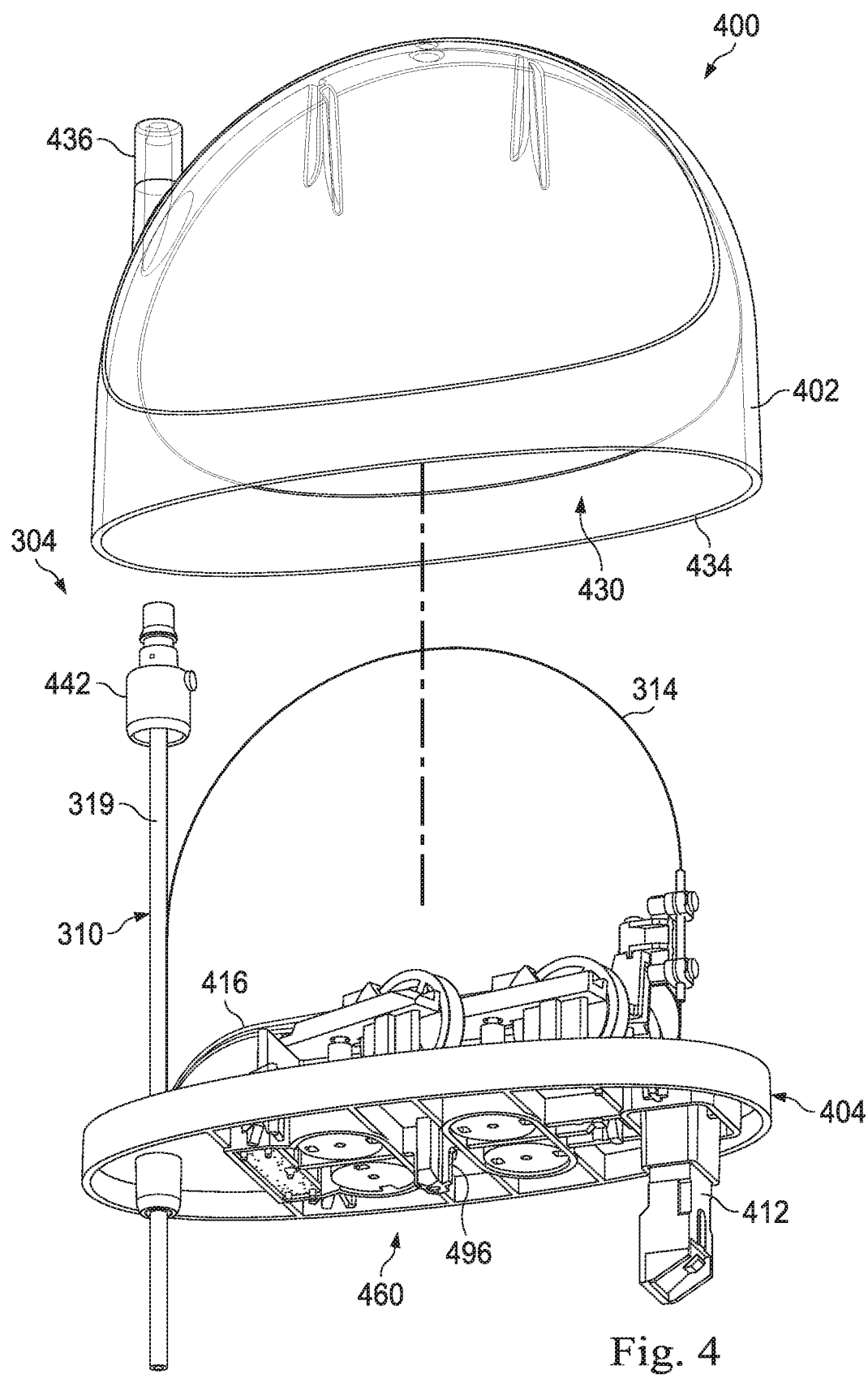
FIG. 4 is diagram of a backend mechanism of a medical instrument in a partially exploded configuration according to some embodiments.
Figure 8:
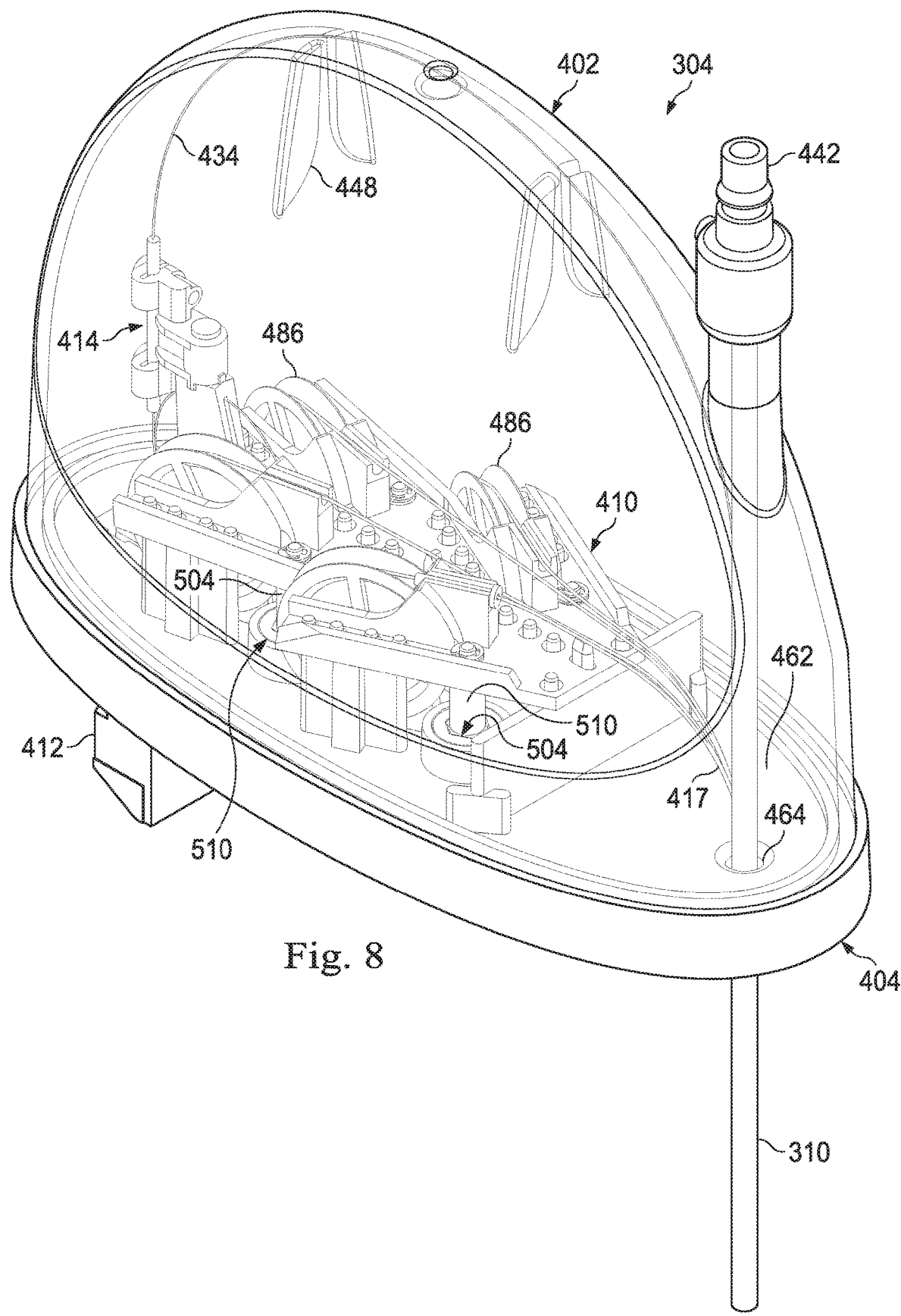
FIG. 8 is a diagram of a backend mechanism of a medical instrument according to some embodiments.

FIGS. 4, 5, and 8 are perspective views of the backend mechanism 304 independent of the instrument carriage 306 from FIGS. 3A and 3B, and including a proximal portion 319 of the elongate member 310. FIG. 4 shows the backend mechanism 304 in a partially exploded state, and FIG. 5 shows a portion of the backend mechanism 304 in a more fully exploded state. FIG. 8 shows the backend mechanism 304 in an assembled state, with a portion of a housing 400 as transparent. Referring to these Figures, the backend mechanism 304 includes the housing 400, including a cover 402 and a chassis 404. For ease of visualization, the cover 402 is not shown in FIG. 5. The chassis 404 carries a plurality of steering components 406, a plurality of drive components 408, a support fixture 410, a fiber connector 412, and a launch region fixture 414. The proximal portion 319 of the elongate member 310 extends through and terminates within the housing 400. FIGS. 4 and 5 also show the shape sensor 314 extending from the proximal portion 319 of the elongate member 310 to the launch region fixture 414 and show a plurality of coil pipes 417 with pull wires 416 disposed therein extending from the elongate member. The coil pipes 417 and the pull wires 416 also extend from the elongate member 310 to the plurality of steering components 406. The housing 400, including the cover 402 and the chassis 404, is selectively attachable to the instrument carriage 306 (FIGS. 3A and 3B) and provides a compact manageable unit that securely protects steering and sensing components from the surgical environment. In some implementations, the coil pipe 417 may have a terminal proximal end fixed relative to the support fixture 410. The pull wire 416 may extend through a lumen in the coil pipe 417, extend from the terminal proximal end of the coil pipe 417, and route around steering component 406 and drive component 408.

Figure 7:
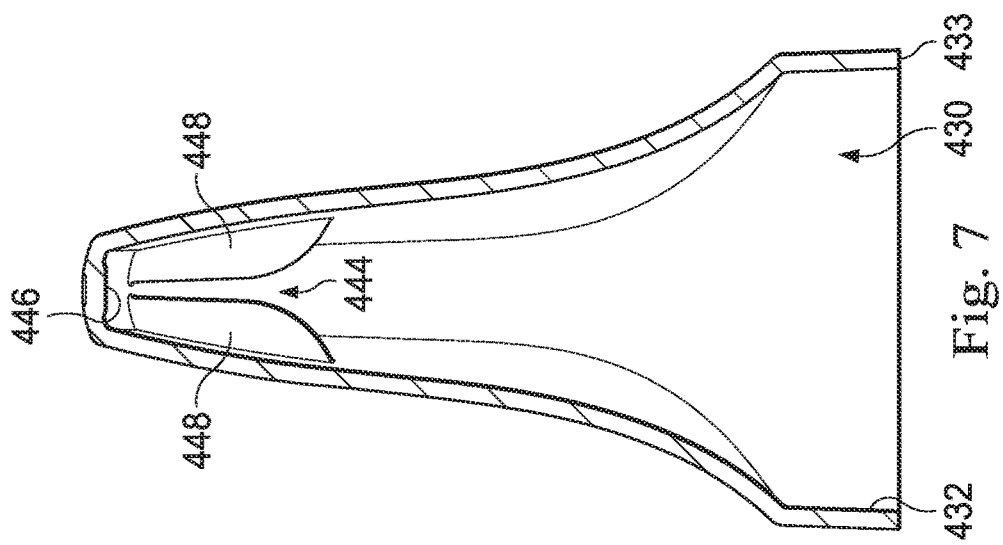
FIG. 7 is a cross-sectional diagram along lines 7-7 in FIG. 6 of the housing according to some embodiments.
Figure 6:
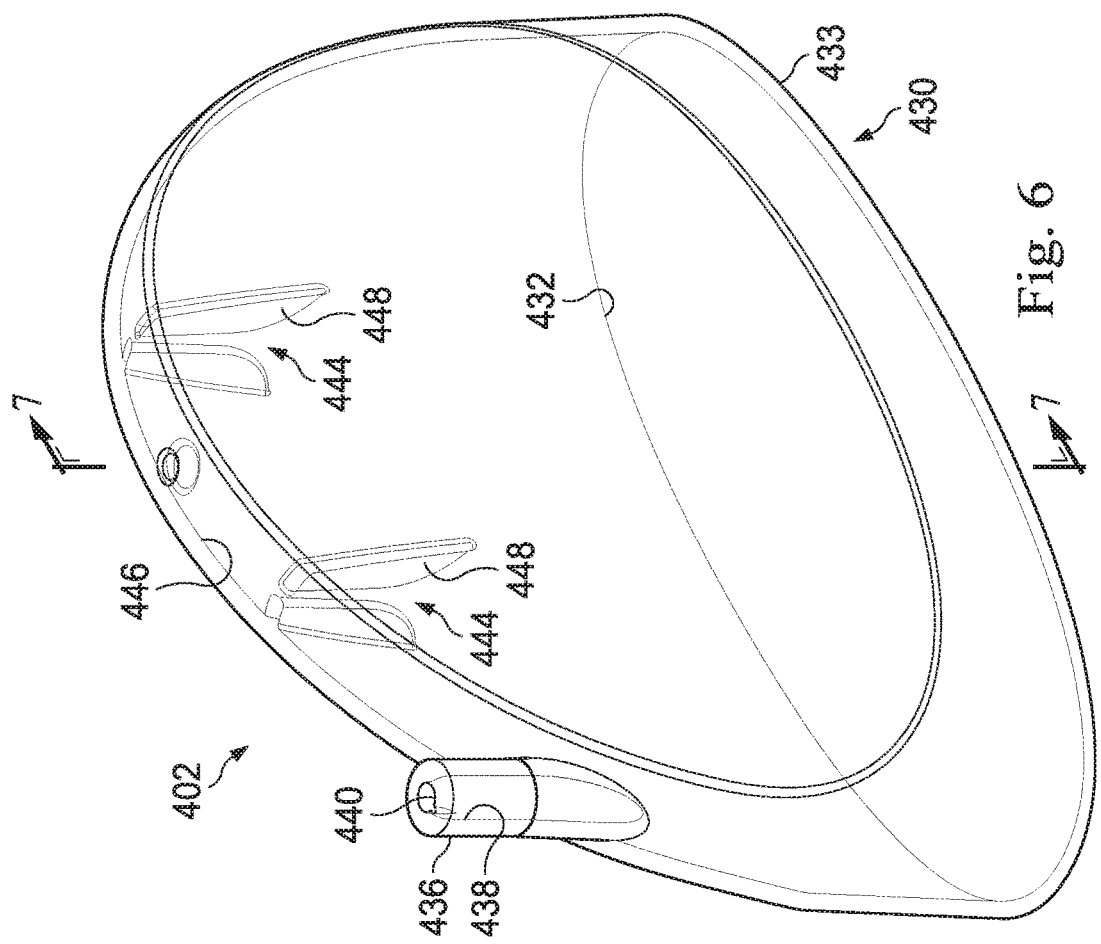
FIG. 6 is a diagram of a portion of a housing of a backend mechanism of a medical instrument according to some embodiments.

The cover 402 is shown in FIGS. 4, 6, and 7. FIG. 6 shows the cover 402 in a transparent view independent of the chassis and components carried by the chassis. FIG. 7 shows a cross-sectional view of the cover 402, taken along the line 7-7 in FIG. 6. The cover 402 may comprise a cavity 430 sized and arranged to cover and protect the steering components 406, the drive components 408, and other components carried by the chassis 404. An opening 432 to the cavity 430 is defined by edges 433 shaped to interface with the chassis 404. In the implementation shown, the cover 402 comprises a protruding boss 436 extending in a direction opposite the opening 432. In this implementation, the protruding boss 436 comprises a passage 438 through which the elongate member 310 may extend. Some exemplary implementations of the protruding boss 436 comprise connection features, such as one or more helical threads, that cooperate with a corresponding connection feature, such as a thread, of a portion of the elongate member 310. Referring to FIGS. 4 and 5, the elongate member is shown to include a locking connector 442 at the proximal portion 319. In some embodiments, the locking connector 442 is a luer fitting or other connector arranged to interface with the proximal portion 319 of the elongate member 310. The locking connector 442 may permit connection to other medical device components.

In the implementation shown, the cover 402 comprises internal curved service loop guide slots 444 that guide and constrain the shape sensor 314 when it is shaped to form a service loop 434 (FIG. 8) while allowing for varying length or slack of the shape sensor from the launch region fixture 414 to proximal portion of elongate member 310. In other words, the internal guide slots 444 provide for a varying radius and height of the service loop 434 of the shape sensor 314. The varying slack occurs because the fiber is located off the elongated member centerline or neutral axis of bending so that as the catheter bends, the fiber is forced to telescope in and out of its lumen in the elongated flexible shaft. Depending upon the implementation, it may be important for shape sensing accuracy that the shape sensor 314, which as described above may be an optical fiber, does not experience tight bends within its shape sensing section. Additionally, the shape sensor may experience failure if bent in a tight radius. In some implementations, the service loop 434 may extend from the launch region fixture 414, through the guide slots 444, and into the proximal portion 319 of the elongate member 310, and to the distal end 318 of the elongate member 310 (FIGS. 3A and 3B). In some implementations, tight bends may interrupt the measurable strain elements of the shape sensor 314 portion forming the service loop 434 leading to less accurate and less predictable sensing of the data. Likewise, this can lead to reduced accuracy in determining the location of the distal end of the elongate member 310.

The internal guide slots 444 in the cover 402 support the service loop 434 in a smooth, sufficiently sized arc from where it exits the proximal portion 319 of the elongate member 310 and curves to terminate in the launch region fixture 414. In this implementation, the internal guide slots 444 enable the service loop 434 to curve 180° from the elongate member to the launch region fixture 414. Accordingly, and as best seen in FIG. 7, the guide slot 444 guides the service loop 434 along a smooth arcing surface 446 along which the shape sensor 314 may be disposed. In some implementations, the shape sensor 314 may be naturally biased toward a straight configuration. Accordingly, the service loop 434 may curve from the launch region fixture 414 to the elongate member 310. In the implementation shown, the internal guide slots 444 are also defined in part by one or more stabilizing guides or stabilizing guide rib sets 448. The implementation shown includes two stabilizing guide rib sets 448, spaced along the arcing surface 446 in the cavity 430. The stabilizing guide rib sets 448 form the narrow opening of the guide slots 444 through which the service loop 434 may extend. In some implementations, the narrow opening may have a width just slightly greater than a diameter of the shape sensor 314. In this way, the shape sensor 314 may be maintained in place, while minimizing lateral movement of the shape sensor 314 in a manner that might disrupt or decrease the accuracy of the measured position of the elongate member 310. Here, the stabilizing guide rib sets 448 have a minimal thickness and extend from arcing surface 446 toward the opening 432 of the cover 402. In some implementations, the cover 402 is shaped to provide a fin, with the fin accommodating the service loop 434. In some implementations, the service loop 434 is asymmetrical. In some implementations, the guide slots 444 and the arcing surface 446 cooperate with the elongate member 310 and the launch region fixture 414 to maintain the shape sensor with a loop having a minimum 180° arc angle. Implementations having an arc angle of 180 degrees may align the fiber connector and the elongate device so as to be parallel to each other. Accordingly, coupling of the backend mechanism may be simplified because the operator simply pushes in the elongate member 310, then engages the fiber connector 412, and then pushes in on kinematic mounts (described below). In some implementations, the loop formed may have an arc angle greater than 180°. For example, depending upon the implementation, the loop may fall within an arc angle in a range of 90-270 degrees, although other arc ranges, both larger and smaller are contemplated. Some alternate embodiments may have the fiber connector perpendicular to the catheter input, in which case, the arc angle may be about 90 degrees.

In some implementations, the cover 402 may serve as a handler gripping surface for the backend mechanism 304. Accordingly, it may be shaped and sized for convenient grasping by a human hand.

The chassis 404 is arranged to support components of the backend mechanism 304. For example, the chassis 404 may support the steering components 406, drive components 408, the support fixture 410, the fiber connector 412, and the launch region fixture 414. The chassis 404 may include a mounting face 460 and an opposing steering components support face 462. A plurality of openings extends through the chassis 404 from the steering components support face 462 to the mounting face 460. For example, the chassis 404 includes an elongate member opening 464, drive component openings 466, and a fiber connector opening 468. The elongate member 310 extends through the elongate member opening 464, the drive components 408 extend through the drive component openings 466, and the fiber connector 412 extends through the fiber connector opening 468. These openings may be used to provide electrical or mechanical connection between components forming an outer portion of the backend mechanism 304 and components disposed within the housing 400 of the backend mechanism 304. The mounting face 460 may be arranged to interface with the instrument carriage 306. In some implementations, the instrument carriage 306 may include drive mechanisms such as drive motors, which interface with and drive the drive components 408 of the backend mechanism 304 and may include pin or other connectors that may provide an electrical communication interface that may interface with the printed circuit assembly 806 (FIG. 10), for example.

Figure 9:
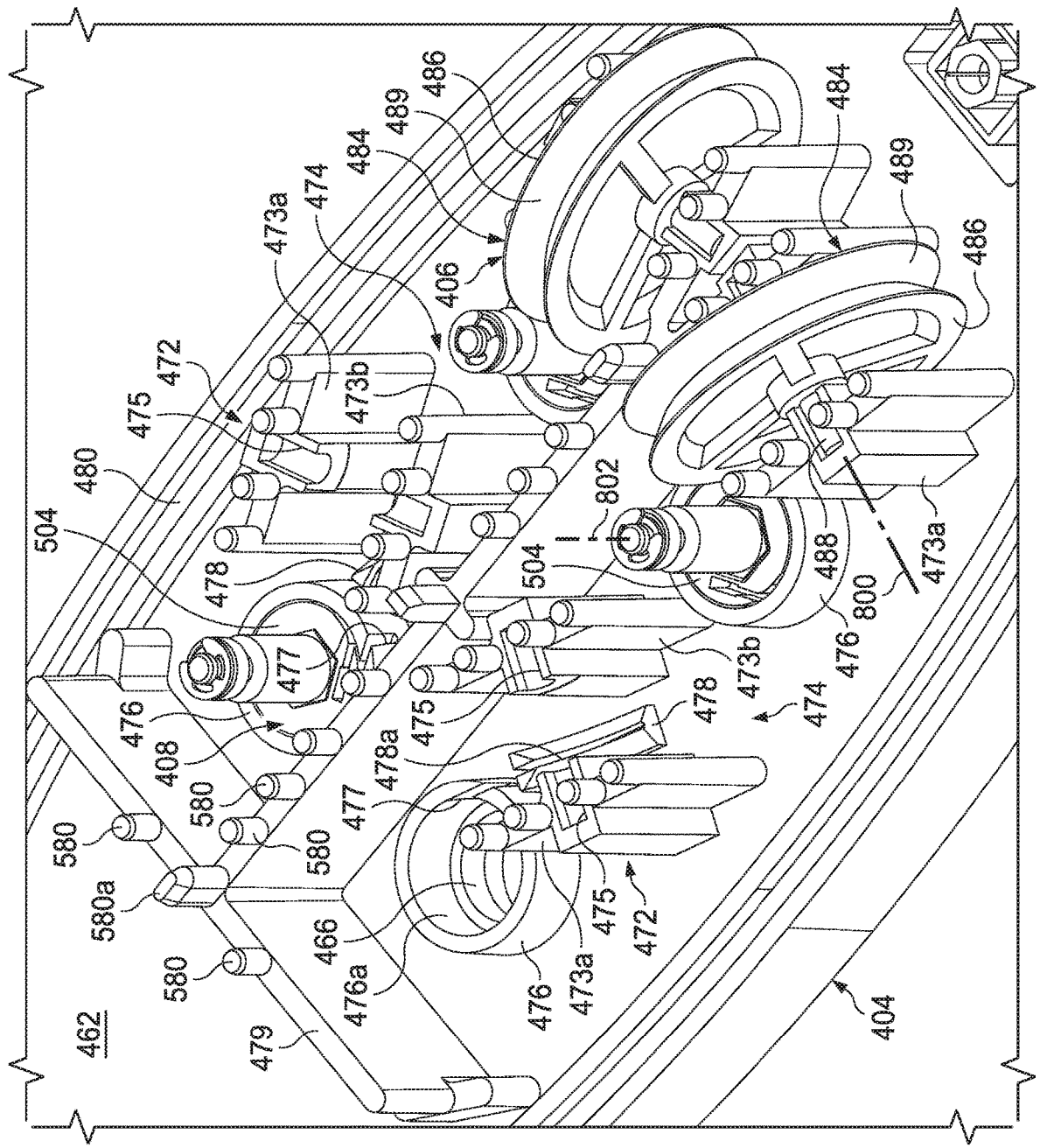
FIG. 9 is a diagram of a portion of a chassis of a backend mechanism of a medical instrument according to some embodiments.

FIG. 9 shows the steering component support face 462 in greater detail. Referring to both FIGS. 5 and 9, the steering components support face 462 comprises a plurality of projecting bosses and features shaped and arranged to support the steering components 406, the drive components 408, and the support fixture 410. In this implementation, the steering components support face 462 includes support projections 472 that each supports a portion of the steering components 406. As best seen in FIG. 9, in this implementation, the support projections 472 may each be made up of a pair of walls 473a, 473b, separated by a gap 474. The walls 473a, 473b each comprise a trough 475 sized and shaped to support pulley axles, and a pulley wheel 486 may be disposed in the gap 474 as will be described below.

In the implementation shown, the support projections 472 are disposed adjacent one of the drive component openings 466. Each drive component opening 466 is surrounded by a circular wall of the chassis 404 forming a pocket 476. The pocket 476 stabilizes and secures components, such as the drive components 408, in place. The circular wall forming the pocket has an inner diameter that may be sized to cooperate with at least a portion of the steering components 406 to prevent the pull wire from pulling free or separating from the steering components as discussed below. In this implementation, each pocket 476 includes a slit 477 that is sized with a width sufficient for passage of one of the pull wires 416. The slit 477 faces or is aligned with the gap 474 between the walls 473a, 473b of the support projections 472. It also faces an alignment projection 478. The alignment projection 478 includes a slit 478a aligned with the slit 477 for the passage of the pull wire. It is shaped to fit adjacent a wheel of a pulley, and is configured to prevent the pull wire from coming off the pulley, even when the pull wire may have slack. In this implementation, the alignment projection 478 is shaped to fit within a groove of the pulley while allowing the pull wire to extend from the pulley, through the slit 478a of alignment projection 478, through the slit 477 and to a capstan forming a part of the drive components 408.

A front wall 479 is disposed between the elongate member opening 464 and the other openings. The implementation shown, the steering components support face 462 of the chassis 404 comprises a peripheral groove 480 that may receive the edge 433 of the cover 402. In some implementations, the peripheral groove 480 and the edge 433 may cooperate to shield or seal and prevent ingress of fluid into the housing 400. In other implementations, the chassis 404 may include a projecting edge and the cover 402 may include a receiving groove that receives the projecting edge of the chassis. Other shielding or sealing arrangements are contemplated.

The steering components 406 are arranged to direct the pull wires 416 that extend from the elongate member 310 to the drive components 408. The pull wires 416 may be axially tightened or loosened to displace the distal end 318 of the elongate member 310 as described above. Each steering component 406 includes a pulley 484 including a wheel 486 and an axle 488. In this implementation, the axle is arranged substantially orthogonal to the axis of the proximal portion 319 of the elongated member 310. Here, the axle 488 defines the axis about which the wheel 486 rotates. The wheel 486 may be formed of a low friction pulley material to enable free rotation about the axle 488. In some implementations, the low friction pulley material is a metal, such as stainless steel or aluminum with a low friction bearing, while in other implementations, the low friction pulley material is a polymer material such as, without limitation, polyethylene terephthalate (PET), acetal (POM), polyamides, and others, all of which may optionally be enhanced by compounded or applied lubricants such as PTFE, silicone oil, paraffin wax and others. The wheel 486 may include a deep, v-shaped pull wire supporting surface, shown and referred to herein as a groove 489 configured to recapture slack loop in the pull wires including when the slack loop deviates from the pulley groove centerline beyond the outer wall of the pulley wheel. In addition, the groove 489 may be wide to assist in capture. In some implementations, slack in the pull wires may be created during bending of the elongate member 310. The width of the groove 489 may re-direct the pull wire onto the wheel 486 even if the slack temporarily removes the pull wire from the groove 489. In some implementations, the pull wire may have a diameter in a range of about 0.015 to about 0.003 inches. The groove 489 may have a width of about 0.070 to about 0.250, although larger and smaller grooves are contemplated. In some implementations, a ratio of the pull wire diameter to the groove with is about 27 to 1. In some implementations, the width of the groove 489 may be in a range of about 10% to about 30% of the diameter of the wheel 486. However, other diameters and widths and ratios are contemplated. In some implementations, the pull wire may have a bend that causes lateral displacement when the pull wire has slack. The wide groove may assist with recapture of the pull wire into the groove 489. The groove 489 may be aligned with a tangent reference line intersecting with the axis of the elongate member 310 or may be offset from it. The axle 488 may be supported at each end on the support projections 472 of the chassis 404. Some implementations of the groove 489 are V-shaped. Some of these implementations may include a 90 degree V-shaped groove.

Other implementations may include a V-shaped groove having an angle that may be between about 45 degrees and 135 degrees. Still others are contemplated. The groove 489 may be sized so as to be wide enough that even slack on the wire will auto-return to stay on the wheel 486. In some implementations, a ratio of a pitch diameter of the groove 489 to a pull wire diameter may be within a range of about 35:1 to about 10:1. Other size ratios however are contemplated.

The drive components 408 (FIG. 5) may interface with the pull wires 416 and may be driven by motors on the instrument carriage 306. Accordingly, the drive components 408 may increase and decrease tension in the pull wires 416 to effect movement at the distal end 318 of the elongate member 310. In the implementation shown, each drive component 408 may include an input disk 500 with an axially extending shaft 510, a capstan 504, and a rotation limit ring 516. In some implementations, a centrally disposed lock shaft 506 extends through the central opening in the axially extending shaft 510 and capstan 504.

Figure 10:
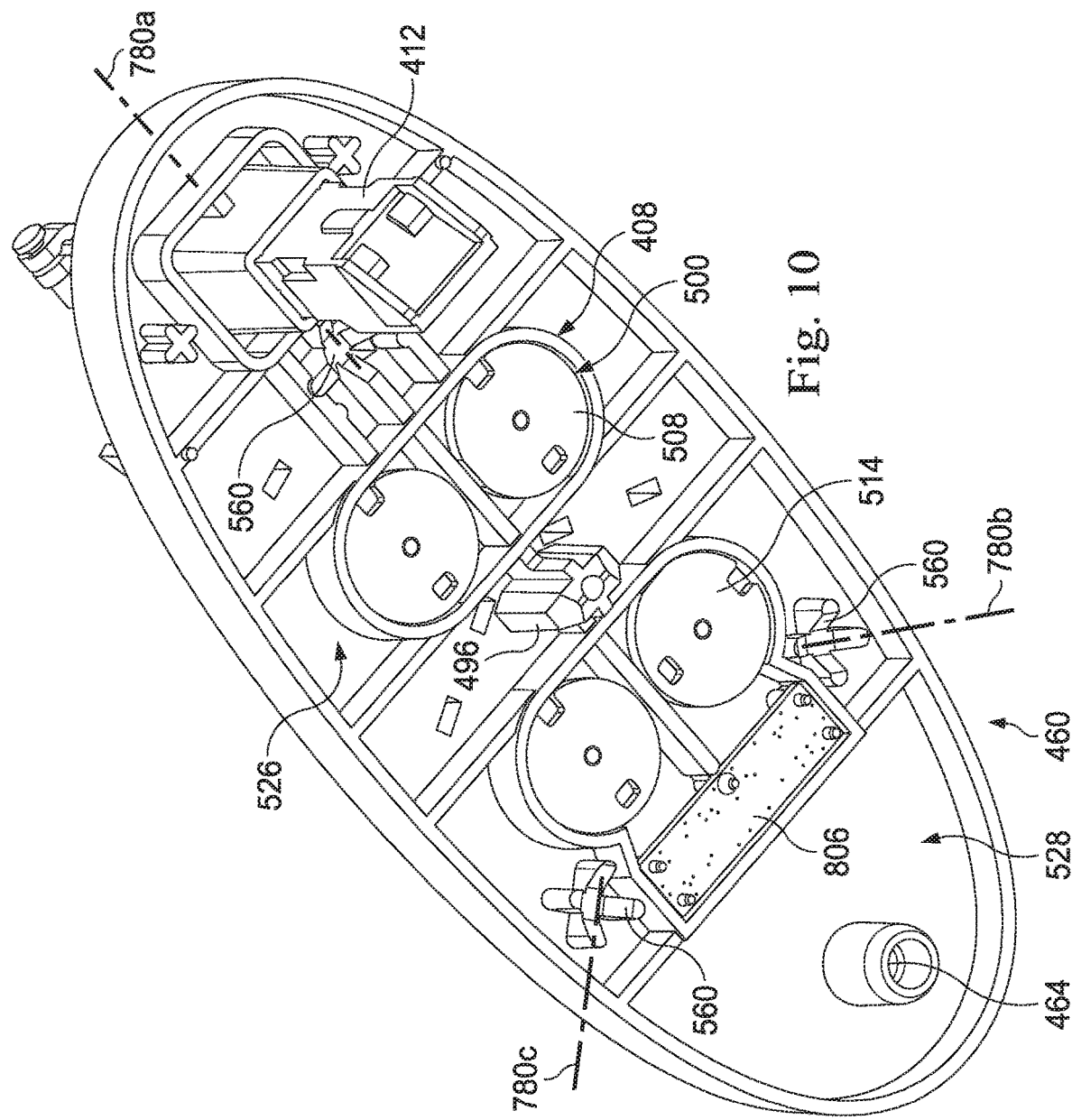
FIG. 10 is a diagram of a mounting face of the chassis of a backend mechanism of a medical instrument according to some embodiments.
Figure 11:
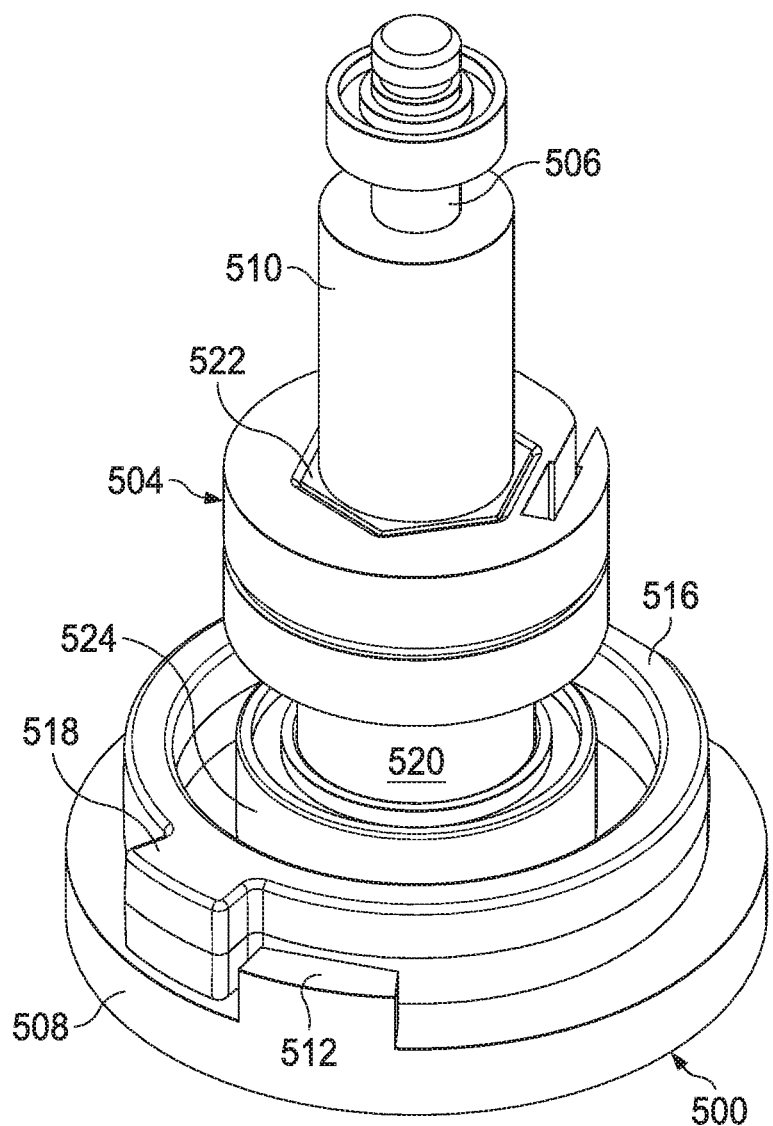
FIG. 11 is a diagram of a drive component for a backend mechanism of a medical instrument according to some embodiments.
Figure 12:
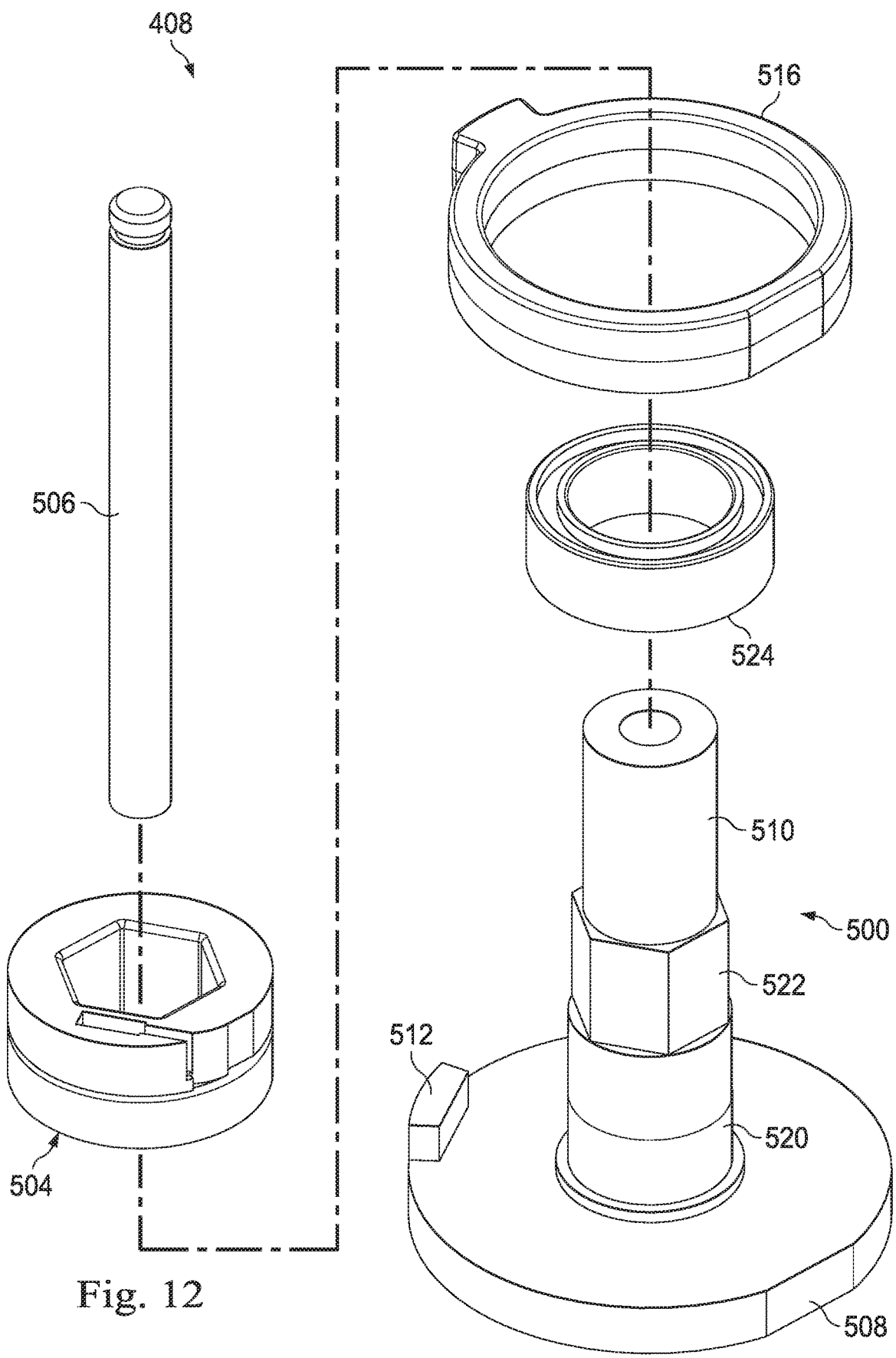
FIG. 12 is a diagram of a drive component in an exploded configuration for a backend mechanism of a medical instrument according to some embodiments.
Figure 13:
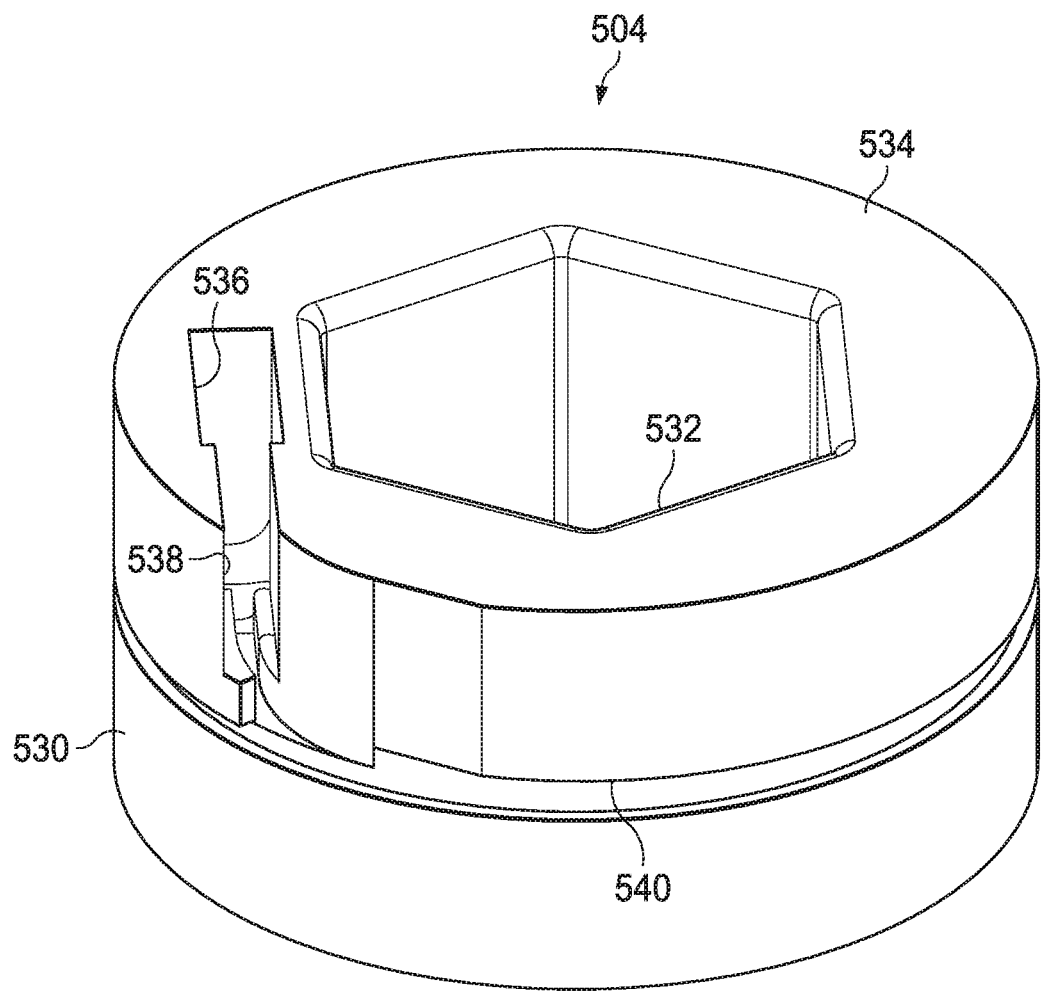
FIG. 13 is a diagram of a capstan for a backend mechanism of a medical instrument according to some embodiments.

FIGS. 11-13 show the drive components 408 in greater detail. FIG. 10 shows a bottom perspective view of the backend mechanism 304 with the input disks 500 readily visible. FIG. 11 shows a single drive component 408 including the input disk 500 and the capstan 504 in an assembled state. FIG. 12 shows a single drive component 408 including the input disk 500 and the capstan 504 in an exploded state. FIG. 13 shows the capstan 504 independent of other drive component elements.

Referring to these Figures, the input disks 500, which may also be referred to as input members, are configured to interface with corresponding output disks (not shown) on the instrument carriage 306 (FIGS. 3A and 3B). The input disk 500 may comprise a head 508 and an axially extending shaft portion 510. The shaft portion 510 extends from the head 508. In this implementation, the shaft portion 510 extends through the drive component openings 466 of the chassis 404 from outside of the housing 400 to the steering components support face 462 of the chassis 404. The head 508 of the input disk 500 may be disposed at the mounting face 460 of the chassis 404, and may couple with the output disks on the instrument carriage 306. By coupling the head 508 to the output disks on the instrument carriage 306, rotation of motors on the instrument carriage 306 may provide corresponding rotation of the input disk 500 and the drive components 408.

In some embodiments, the input disk 500 includes a bottom face 514 arranged to interface with and engage a face of a corresponding output disk on the instrument carriage 306 and impart torque from the output disk to the drive component 408. Depending on the implementation, the face 514 may have features that mechanically engage with the output disk, such as pockets, recesses, splines, protrusions or other features that may be used to impart torque to the drive components 408. The head 508 of the input disk 500 also may shield a shaft portion 510 and a bearing 524 (FIG. 12) from fluid ingress. Additional shielding may be due to the shape and extent that the mounting face 460 of the chassis 404 mates with the instrument carriage 306 when the mounting face 460 is mounted to the instrument carriage 306.

Some implementations of the input disks 500 include an axially extending rotation limiter 512. The rotation limiter 512 stops reverse rotational motion of the input disk 500 beyond a threshold position that may bend or break the pull wires 416. In the implementation shown, the rotation limiter 512 is a projection extending upwardly in the direction of the shaft portion 510 from the head 508. When the input disk 500 rotates about an axis of the shaft portion 510, the rotation limiter 512 may engage corresponding protruding rotation stops 518 on the rotation limit ring 516. The rotation limiter 512 and rotation limit ring 516 may be particularly positioned to permit sufficient rotation to provide steering by tensioning or de-tensioning the pull wire 416, while preventing over-rotation in either the forward or reverse rotating direction in a manner that might put excessive stress on weak points. In particular, rotation limiter 512 in conjunction with rotation limit ring 516 allows greater than one rotation of input disk 500 while limiting the rotation to protect the mechanism. Furthermore, the input rotation limiter 512 may protect the pull wires and internal mechanisms from rotation of the inputs while the backend mechanism 304 is disconnected from the motor outputs on the instrument carriage 306. The rotation limiter and limit ring also protects the pull wire and mechanism in the instance that the backend mechanism is removed from instrument carriage 306 while motor torques are applied to one or more of input disks 500.

As best seen in FIG. 11, the protruding rotation stops 518 on the rotation limit ring 516 have a thickness or height greater than the height of the rotation limiter 512. The rotation limiter 512 may have a height selected to mechanically engage the protruding rotation stop 518, without mechanically engaging against a rotation stop fixed to or forming a part of the chassis 404. In contrast, the protruding rotation stop 518 may be sized and positioned to engage both the rotation limiter 512 and a rotation stop fixed to or forming a part of the chassis 404. Because the rotation limit ring 516 may be rotated nearly 360° relative to the chassis 404 before engaging a rotation stop on the chassis 404, and because the input disk 500 may be rotated nearly 360° relative to the rotation limit ring 516, the overall rotation permitted by the input disk 500 relative to the chassis may be greater than 360°, and may be less than 720°. The amount of rotation permitted by the rotation stop arrangement may be varied by adjusting the circumferential thickness of the rotation limiter 512 and the protruding rotation stop 518.

In addition, the rotation limiter 512 may protect the pull wires from rotation of input disks while the instrument is disconnected from the motor outputs. The rotation limiter 512 may also protect pull wires 416 from recoil induced reverse bending if the input disks 500 are disengaged from the instrument carriage 306 while motors are applying torque to the inputs. In some implementations, the rotation limiter may also help prevent derailing of the pull wires from the groove 540 of capstan 504.

The axially extending shaft portion 510 extends from the head 508 and includes a cylindrical portion 520 and a non-cylindrical portion 522. A bearing 524 may be disposed about the cylindrical portion 520. The capstan 504 may be disposed about the non-cylindrical portion 522. The non-cylindrical portion 522 may insure that the capstan 504 is rotationally fixed to the input disk 500. In FIG. 12, the non-cylindrical portion 522 has a hexagonal shape although other polygons, splines, stellated polygons and other non-cylindrical shapes may be used and are contemplated.

FIG. 13 shows the capstan 504. The capstan 504 includes a cylindrical outer surface 530, a non-cylindrical inner surface 532, and an end surface 534. As indicated above, the non-cylindrical inner surface 532 is configured to fit about the non-cylindrical portion 522 of the axially extending shaft portion 510 of the input disk 500. Accordingly, in this implementation, the non-cylindrical inner surface 532 has a hexagonal shape, although other shapes are contemplated.

The end surface 534 includes a crimp slot 536. In this implementation, the crimp slot 536 is shaped to receive a crimped end of one of the pull wires 416. The crimp slot 536 extends axially inward from the end surface 534, and intersects the cylindrical outer surface 530 at a slot opening 538. In this implementation, the crimp slot 536 includes a bulbous portion and a narrow portion. The bulbous portion may be configured to receive a bulbous end of a pull wire 416 including a crimp fitting, with a more narrow portion of the pull wire extending out the slot opening 538. In FIG. 13, the cylindrical outer surface 530 includes a circumferential groove 540. In this implementation, the circumferential groove 540 extends completely around the exterior cylindrical outer surface 530. A portion of the slot opening 538 intersects the circumferential groove 540, and a pull wire 416 may extend from the slot opening 538 and may be wound around the capstan 504 in the circumferential groove 540. In this implementation, the circumferential groove 540 is asymmetrical. That is, one portion of the circumferential groove 540 is wider than another portion of the radial groove. In this manner, the circumferential groove 540 may be configured to accommodate more than a single wrap of a pull wire around the capstan 504. In the implementation shown, the circumferential groove 540 has a width relatively greater at the slot opening 538 and has a width relatively smaller at a location adjacent to but behind the slot opening 538. In some implementations, the circumferential groove 540 may be a helical groove to prevent additional wire wraps from overlapping on each other. Such overlaps can create local high stresses in the pull wire, and in some instances may cause the pull wire to fail.

In this implementation, and as described with reference to FIG. 9, the capstan 504 fits within a pocket 476 formed as a part of the chassis 404. The pocket 476 includes the slit 477 which allows the pull wire 416 to exit the pocket 476 in only one direction toward pulley groove 489 while pocket 476 retains the pull wire 416 in all other directions. As such, even when the backend mechanism 304 is removed from the instrument carriage 306, and therefore there is no torque on the capstan, the pull wire 416 is still maintained in the slit 477 in the chassis 404. In some implementations, the pocket 476 includes an inner wall 476a (FIG. 9) extending around the capstan 504. The inner wall 476a may have a diameter only slightly larger than a diameter of the capstan 504. In some implementations, a gap may be formed between the inner wall 476a of the pocket 476 and the outer periphery 530 of the capstan 504. Depending upon the implementation, this gap may be sized to be no more than two times or twice the diameter of the pull wire and preferably less than a diameter of the pull wire. For example, in implementations using a pull wire of 0.007 inch diameter, the gap between the inner wall 476a of the pocket 476 and the outer periphery of the capstan 504 may be in a range of about 0.007 inch to about 0.005 inch or smaller. This clearance may prevent the pull wire from disengaging from the groove 540 of capstan 504 even when there is slack in the pull wire. Accordingly, the pocket 476 may assist in holding the pull wire on the capstan 504. In the implementation shown, the pocket 476 is monolithically formed as a part of the chassis 404. In particular it is desirable for the gap to be less than or equal to 2 times of the pull wire diameter. Preferred implementations have a gap sized less than or equal to the pull wire diameter. Other preferred implementations have a gap less than or equal to about twice the diameter of the pull wire.

Figure 17:
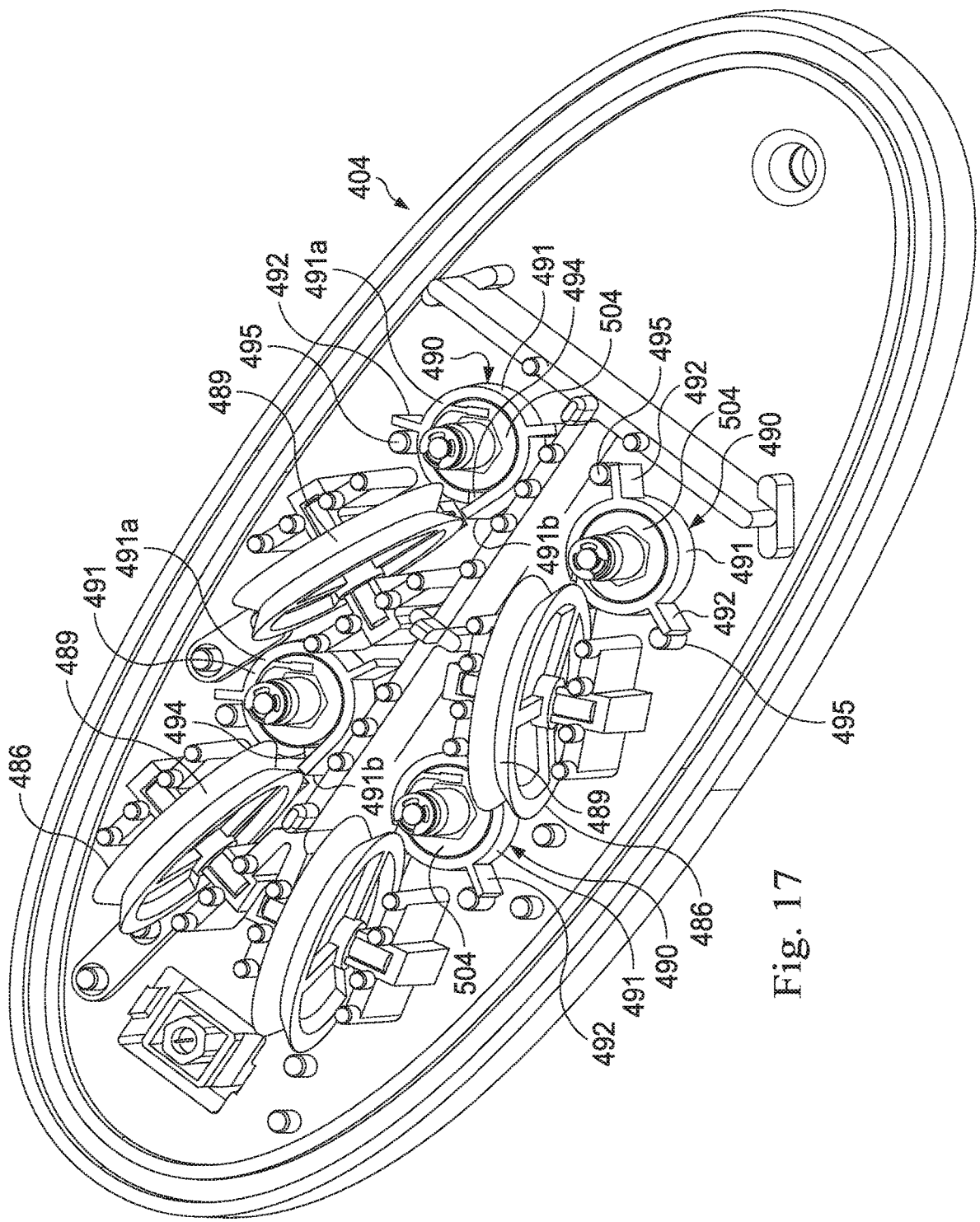
FIG. 17 is a diagram of a portion of a chassis of a backend mechanism of a medical instrument according to some embodiments.

FIG. 17 shows an implementation where the capstan 504 fits within a pocket 490 that is formed as a component separate from the chassis 404. Here, the pocket 490 is referred to as a floating pocket because it is not attached to the chassis 404. In the example shown, the pocket 490 may include a round body 491 formed as a circumferential wall, at least one wing 492 extending outwardly from the body 491, and a slit 494 in the body 491. Here, the body 491 includes a relatively cylindrical inner surface (not labeled) that fits about the periphery of the capstan 504. In some examples, the floating pocket 490 may be in contact with the outer diameter or periphery 530 of the capstan 504. FIG. 17 shows two wings 492 extending radially outwardly from the body 491. These projecting wings 492 may act as mechanical stops that cooperate with components of the chassis or other components to prevent rotation of the pocket 490 with the capstan 504. In this implementation, the chassis 404 includes two projecting stops 495 each placed to mechanically interfere with one of the wings 492 to limit the rotation of the pocket 490 in one direction. Working together, the projecting stops 495 and the wings 492 limit or prevent rotation so that the slit 494 remains substantially aligned with the slit 478a of the alignment projection 478 that cooperates with the wheel 486 of the pulley 484. The slit 478a may be also be referenced as a pull wire exit gap. In the implementation shown the slit 494 extends the axial length of the pocket 490. Accordingly the slit 494 may permit the pocket 490 to flex, thereby elastically changing its inner diameter. Some implementations of the floating pocket 490 may be sized or elastically formed to have a relatively low friction that allows the capstan 504 to rotate within the floating pocket 490. By so doing, the slit 494 may still align with the wheel 486 even as the capstan 504 rotates within the pocket 490.

In some implementations, the pocket 490 is sized in a natural state with an inner diameter slightly smaller than a diameter of the capstan so that the inner wall of the pocket 490 is in contact with the outer periphery 530 of the capstan 504. Because of the elastic nature of the pocket 490, the capstan may rotate relative to the pocket 490. The close fit however may prevent the pull wire from disengaging from the capstan 504 even when there is slack in the pull wire. Accordingly, the pocket 490 may assist in holding the pull wire in groove 540 on the capstan 504. In some implementations, the pocket 490 is configured to maintain a light spring contact around substantially the full circumference of the capstan to hold the pull wire in groove 540 on the capstan 504.

In the example shown, the body 491 of the pocket 490 is shaped as a rolled strip with ends forming the slit 494. The shape of body 491 can also be molded from a compliant low friction plastic material which advantageously reduces contact force, friction coefficient and resulting friction drag torque on capstan 504. The overlap of one end over the other forms a shape of a "6" with a curved portion 491a forming the substantially cylindrical body 491 and a linear portion 491b extending from a tangent of the circle at the slit 494. However, other shapes are contemplated. For example, in another aspect, body 491 may make contact with capstan 504 at intervals spaced along the periphery of 504.

FIG. 9 shows the chassis 404 with the capstan 504 in place relative to the pulley 484. The axle 488 of the pulley 484 defines a rotational axis 800 that is orthogonal to an axis 802 of rotation of the capstan 504. In this embodiment, the axis of rotation of the capstan 504 is also substantially parallel to the longitudinal axis of the elongate member 202. Because of this, the axis of rotation of the pulley 484 is substantially orthogonal to the longitudinal axis of the elongate member.

Figure 14:
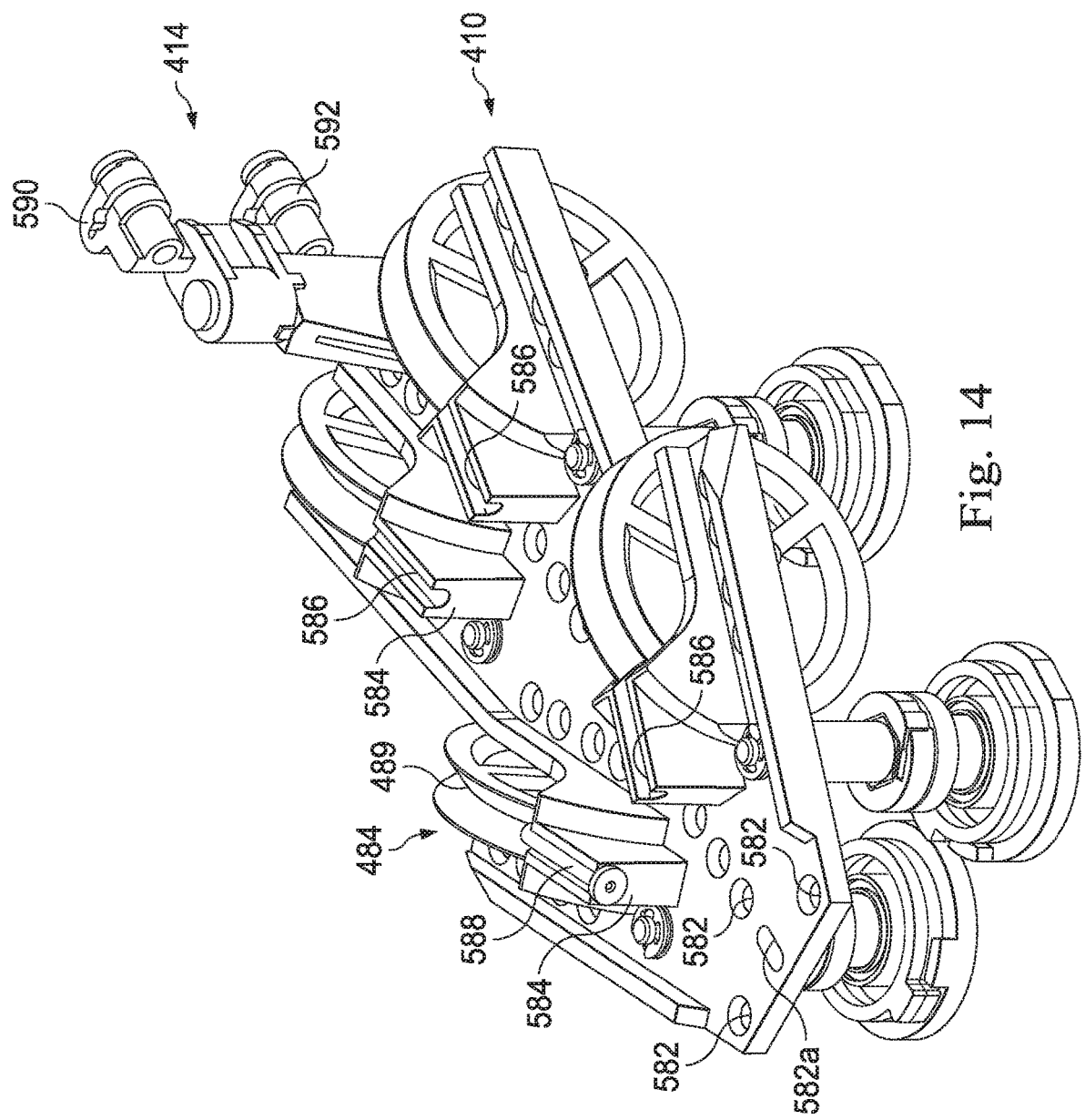
FIG. 14 is a diagram of a partial assembly of a backend mechanism of a medical instrument according to some embodiments.

FIG. 14 shows additional details of the support fixture 410. In this embodiment, the support fixture 410 is arranged to attach to the chassis 404 to secure in place the steering components 406 and the drive components 408. In the particular embodiment shown, alignment elements 580 (FIG. 9), shown as projecting nubs or posts, are disposed on the chassis 404 to cooperate with alignment elements 582 (FIG. 14) shown as notches or nub-receiving apertures on the support fixture 410. In some implementations, the elongated posts 580a of the alignment elements 580 in FIG. 9 engage the elongated holes 582a shown of the alignment elements 582 in FIG. 14 to align support fixture 410 precisely with chassis 404. The circular nubs of the alignment elements 580 in FIG. 9 engage circular holes of the alignment elements in FIG. 14 and are heat staked into the countersinks of the circular holes in FIG. 14 to fasten the support fixture 410 to the chassis 404. With the support fixture 410 in place, the axle 488 of the pulley 484 is secured in the trough 475 of the support projections 472. Likewise, the drive component 408 may be secured in place to the support fixture 410.

In the implementation shown, the support fixture 410 also includes a coil pipe mount 584 arranged to retain coil pipe 417 and align the pull wire 416 with the groove 489 in the pulley 484 so that the pull wire is arranged at an elevation corresponding with the bottom of the groove in the pulley 484. The coil pipe mount 584 may be monolithically formed in the support fixture 410, and in this implementation, includes a trough 586 sized and arranged to receive a tubular pipe element 588 arranged to interface with a coil pipe 417 that extends to the distal end of the elongate member 310. For ease of explanation, only one tubular pipe element 588 is shown in FIG. 14. The tubular pipe element 588 includes an inner passage inside which the coil pipe 417 is bonded while the pull wire extends through both to the groove 489 of the wheel 486 of the pulley 484. The coil pipe 417 is fastened at the coil pipe mount 584, which prevents the coil pipe from proximal translation towards pulley 484.

Returning now to FIG. 5, the fiber connector 412 projects from the mounting face 460 of the chassis 404. A matching receiving connector (not shown) is disposed on the instrument carriage 306. Fiber connector 412 communicates information from the shape sensor 314 to the instrument carriage 306 and ultimately to the control system 112.

The launch region fixture 414 is shown in FIGS. 5, 8 and 14. The launch region fixture 414 is comprised of a series of stabilizing components arranged to rigidly support the proximal end of the shape sensor 314. In this embodiment, the launch region fixture 414 is attached to a portion of the support fixture 410 and includes two clamps 590 and 592 that pinch the shape sensor 314 to prevent movement or misalignment. In this implementation, the two clamps 590 and 592 are spaced apart from one another along an axis substantially parallel with the axis of the elongate member as it exits the housing 400. Although described as being secured via clamps, in other implementations, the launch region fixture 414 may attach to the shape sensor 314 via an adhesive or other attachment mechanism. From the launch region fixture 414, the shape sensor 314 turns 180° and enters the elongate member 310 as shown in FIG. 4.

Referring now to general operation, it is worth noting that in implementations employing four pull wires 416, each pull wire may be fixed to and extend from a distal end of the elongate member 310, separated along the circumference of the elongate member by 90°. In alternative implementations, any number of pull wires may be employed, each extending from the distal end of the elongate member 310, and spaced apart at varying distances along the circumference of the elongate member depending on the desired steering configuration. While the implementation of a single pull wire will be described herein, it should be noted that the implementation may apply to each of the pull wires actuating elongate member 310. The proximal end of the pull wire may be wrapped around a capstan, described herein. Pull wires that provide articulation in the same axis, such as yaw or pitch, may be wrapped around capstans which are positioned diagonally from one another within the backend mechanism 304. In some implementations, each pull wire 416 runs through the coil pipe 417 which is coupled to a distal section of the elongate member 310. Each coil pipe 417 may be paired with a pull wire 416 and extend the length of the elongate member to a distal portion of the elongate member, and exit the elongate member at a proximal portion. An example of pull wires and coil pipes in the elongate member may be found in U.S. Provisional Patent 62/535,673, filed on Jul. 21, 2017, titled "Flexible Elongate Devices Systems and Methods", which is incorporated herein by reference. In some implementations, the coil pipes, and the pull wires disposed therein, exit the elongate member 310 of the backend mechanism 304. In some implementations, each coil pipe and the pull wire disposed therein travels and bends 90° from the elongate member 310 to the support fixture 410. There, the coil pipe 417 may terminate with the terminal end fixed to the support fixture 410 at the coil pipe mount 584 housing the tubular pipe element 588. Although the coil pipe 417 may terminate passing through and bonded inside the tubular pipe element 588, the pull wire 416 passes through and beyond the tubular pipe element 588, routes around the wheel 486 of the pulley 484, and then wraps around the capstan 504, being ultimately fixed in the crimp slot 536 of the capstan 504. The bend in the coil pipes from the elongate member to the tubular pipe element 588 also provide some slack for pistoning, or axial displacement, that may be induced by bending or steering the elongate member.

As described herein, the capstans 504 are oriented orthogonally from the pulleys 484. This and routing the pull wires 180 degrees around the pulleys may permit large radius bends in the pull wires while still providing a compactly sized backend mechanism 304. In addition, the slit 477 in the wall of the pocket 476, combined with the alignment projection 478 that cooperates with the wheel 486 of the pulley 484, provides support to the pull wires and reduces the risk of the pull wires coming loose and displacing so as to be off-track. Furthermore the alignment of the coil pipes with the tubular pipe element 588 may feed the pull wire into the pulley along the tangent to the pulley groove pitch circle. As such, the coil pipes help align the pull wires into the pulley groove. In some implementations, the coil pipes may be adhered, such as with an adhesive, to the tubular pipe element 588 to secure them in place. Other attachment methods may also be used.

Depending on the implementation, the shape sensor, which in some implementations is an optical fiber, may be integrated into the elongate member by passing through a fiber lumen in the elongate member from the distal end of the elongate member to the proximal portion and terminating in the backend mechanism 304. In some implementations, the fiber exits the elongate member, bends 180°, and passes through the launch region fixture and terminates in the fiber connector. The launch region fixture holds the shape sensor in a known straight configuration that is used during shape sensing as an origin and for calibration. In some implementations, the shape sensor is embedded in a hypotube which is made of a concentric, heavy wall, small inner diameter, metal tube. In some implementations, the hypotube is selected to be a 0.0143 ID×0.020 wall, 304 stainless steel hypotube and a Shore A 40 durometer silicone rubber adhesive/sealant is used to bond the fiber in the hypotube. In some implementations, the proximal portion of the shape sensor is adhered with an adhesive or glue into the hypotube. The shape sensor 314 may obtain shape sensing data from the launch region fixture to the distal end of the elongate member. Furthermore, the service loop 434 may accommodate instances where the shape sensor 314 axially displaces, longitudinally within the elongate member. The service loop 434 may accommodate such displacement or pistoning in examples where the shape sensor 314 may be fixed at a distal portion of the elongate member, and the shape sensor 314 floats within a lumen included in a flexible body of the elongate member, such as flexible body 216 of elongate member 202.

In the implementation shown, and with reference to FIG. 3A, the backend mechanism 304 is mounted to the instrument carriage 306 in an orthogonal orientation. That is, the actuation motors in the instrument carriage 306 are positioned so that their axis of rotation is parallel to the insertion axis of the elongate member 310. As described herein and with reference to FIG. 10, since the mounting face 460 of the chassis 404 includes the face 514 of the input disk 500, the elongate member opening 464, the drive component openings 466 both have parallel axes. That is, each has an axis that extends from the mounting face 460 of the chassis 404. In this implementation, the fiber connector 412 also extends from the mounting face 460 in a direction of the elongate member 310. In some implementations, and referring to FIG. 10, only a portion of the mounting face 460 actually interfaces with the instrument carriage 306. For example, in some implementations, the mounting face 460 includes an interface portion 526 and a non-interface portion 528. The interface portion 526 may be a portion that includes the input disks 500 and the fiber connector 412. The interface portion 526 may abut against the instrument carriage 306 in FIG. 3A. The non-interfacing portion 528 may be side-by-side with the interface portion 526. In this implementation, the non-interface portion 528 includes the elongate member opening 464 through which the elongate member extends. Accordingly, the elongate member 310 may be disposed to project from the non-interface portion of the mounting face 460 beyond a side of the instrument carriage 306 such that the elongate member 310 may extend through the elongate member opening 464 without passing through and without interference by the instrument carriage 306, even while the face 514 of the input disks 500 and the fiber connector 412 engage and interface with the instrument carriage 306. Some implementations include a printed circuit assembly 806 that may communicate with the instrument carriage 306 as well.

Still referring to FIG. 10, the interface portion 526 may include a plurality of mounts 560 configured to engage with the instrument carriage 306. In some implementations, the interface portion 526 includes three mounts 560 shaped and configured to provide a kinematic mount that provides stability and repeatability in positioning and orienting of the backend mechanism in a specific pose. Using a kinematic mount may increase the reliability and accuracy of measurement, even when the backend mechanism is disengaged and re-engaged. In the embodiment shown, the mounts 560 of the mounting face 460 are formed of V-shaped grooves or slots that each receives a corresponding ball or hemispherical shaped head on the instrument carriage 306. The three balls (or hemispherical shaped heads) and V-shaped grooves cooperate for repeatable and stable mounting of the backend mechanism. In the implementation shown, each of the mounts 560 comprises two intersecting orthogonally oriented V-shaped grooves that together form a depression or pocket that receives a ball (or hemispherical shaped head). In the example embodiment shown, one of the V-shaped grooves of each mount 560 is wider or angled differently than the corresponding other V-shaped groove. The wider V-shape groove may permit the ball or hemispherical shaped head to easily enter the depression or pocket formed by the V-shaped grooves. The narrower V-shaped groove may guide the ball or hemispherical shaped head to a precise position relative to the instrument carriage 306. Because of this, the kinematic mounts repeatable, precise positioning of the backend mechanism relative to the instrument carriage 306. For reference, FIG. 10 includes three reference axes 780a, 780b, and 780c, each aligned with the narrower V-shaped groove of the three mounts 560. As can be seen, the reference axes 780a, 780b, and 780c each extend in a different direction, thereby providing stability to the kinematic mount, while at the same time, each of the intersecting, orthogonal V-shaped grooves permit easy alignment that guides the ball or hemispherical he shaped head into the more narrow stabilizing V-shaped groove. The misalignment of the three reference axes 780a, 780b, and 780c prevent undesired displacement in six degrees of freedom.

Figure 15:
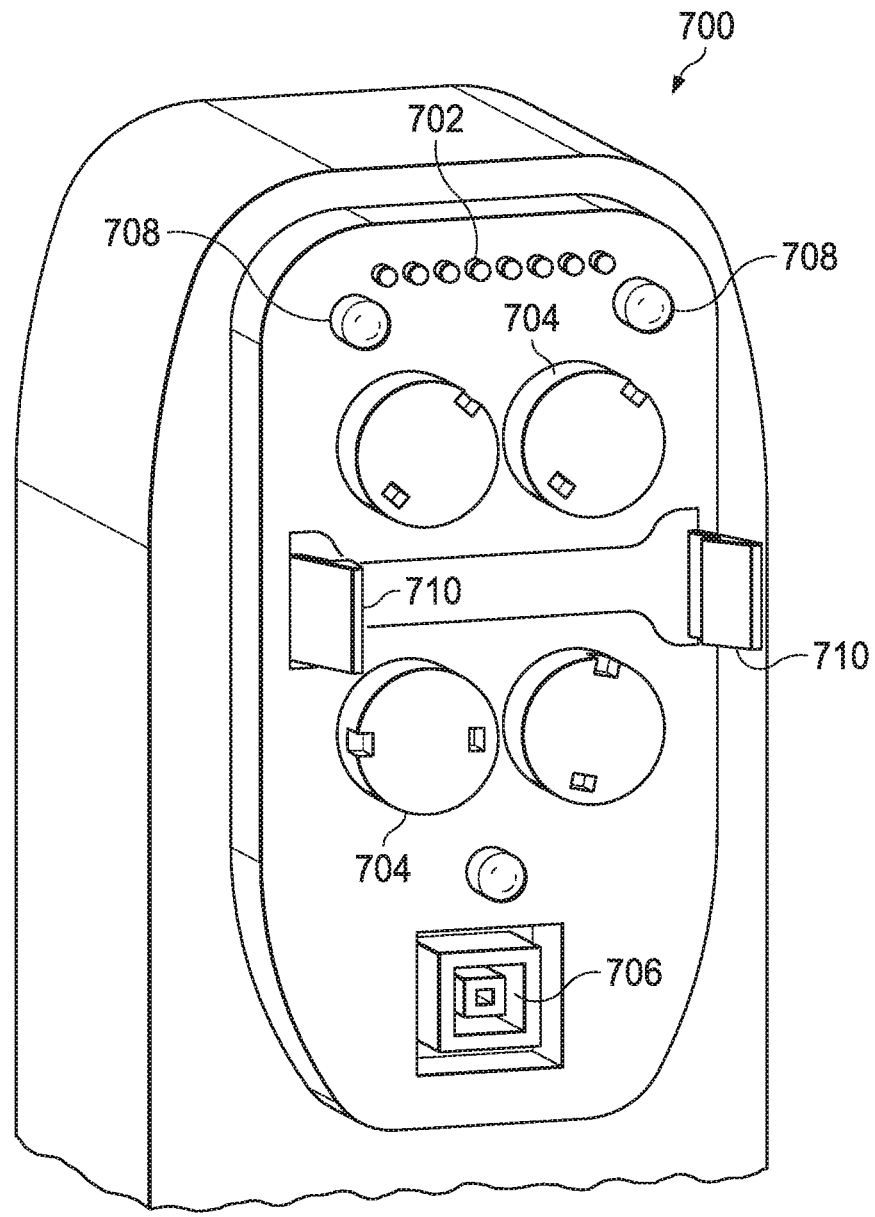
FIG. 15 is a diagram of a portion of an instrument carriage of a medical instrument according to some embodiments.
Figure 16:
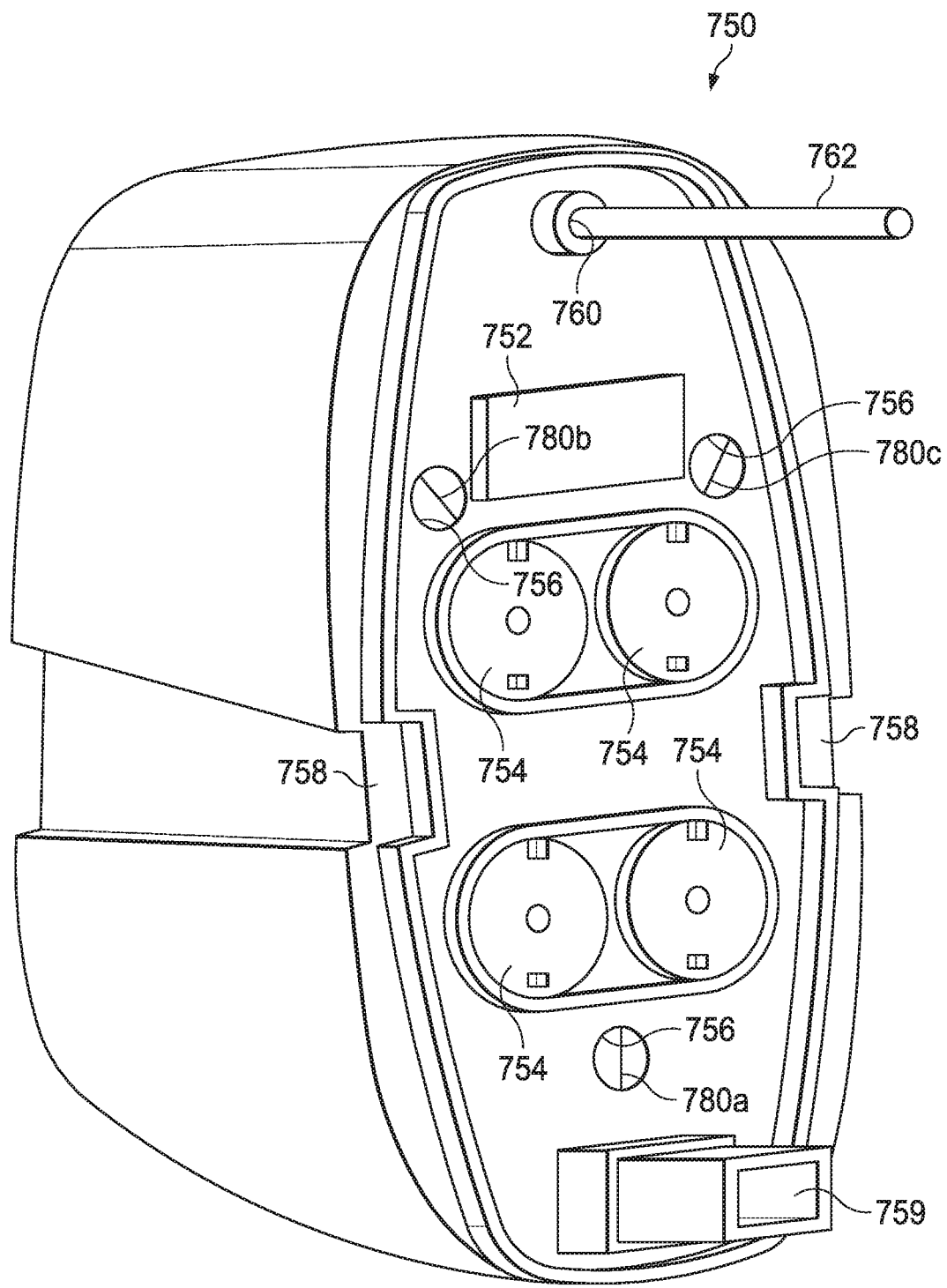
FIG. 16 is a diagram of a backend mechanism of a medical instrument according to some embodiments.

FIGS. 15 and 16 show other implementation and view of an instrument carriage 700 and a backend mechanism 750. The principles and teachings of the instrument carriage 700 and the backend mechanism 750 may be implemented and included in the instrument carriage 306 and the backend mechanism 304.

The instrument carriage 700 in FIG. 15 includes a plurality of pogo pins 702 that may communicate with the printed circuit assembly on the backend mechanism 750. It also includes output disks 704, a female fiber connector 706, kinematic mount components 708, and latch levers 710. The output disks 704 may be driven by motors carried on the instrument carriage 700, and may engage the input disks of the backend mechanism. The female fiber connector 706 may receive the projecting fiber connector on the backend mechanism, and the kinematic mount components 708 may be shaped and configured to engage corresponding kinematic mount components on the backend mechanism. In this implementation, the kinematic mount components 708 are balls or hemispheres fixedly disposed to engage V groove slots on the backend mechanism. The latch levers 710 may project from corresponding sides of the instrument carriage 700, and may be configured to engage and secure the backend mechanism to the instrument carriage.

The backend mechanism 750 in FIG. 16 has a mounting face 751 that includes a printed circuit assembly 752, input disks 754, mounts 756, carriage latch connectors 758, and a fiber connector 759. The printed circuit assembly 752 may communicate with the pogo pins 702 on the instrument carriage 700. The input disks 754 may engage and be driven by the output disks 704. The mounts 756 may be V-shaped grooves arranged to receive the kinematic mount components 708 on the instrument carriage 700. The carriage latch connectors 758 are shown as slots that receive the latch levers 710. In this embodiment, the carriage latch connectors 758 are disposed on opposing sides of the backend mechanism 750. In addition, the latch levers 710 may include connectors, such as arrowhead shaped elements, and the carriage latch connector 758 may include shoulders configured to engage the arrowhead shaped elements in a manner that enables the backend mechanism 750 to be snapped in place on the instrument carriage 700. Other connectors are contemplated. In some implementations, the latch connectors are disposed outside the sealed area so as to prevent the ingress of fluids. In some aspect, the connectors comprise a shield or seal that prevents the ingress of fluids. In some implementations, connection may be carried out by a user with one hand. As can be seen, the mounting face of the backend mechanism 750 includes an elongated member opening 760 through which an elongated member 762 extends. As described and shown in other implementations herein, the mounting face 751 has an interfacing portion and a non-interfacing portion, with the elongated member opening 760 and the non-interfacing portion. That is, when the pogo pins of the instrument carriage 700 are aligned with the circuit assembly 752 of the backend mechanism 750, the non-interfacing portion of the mounting face 751 projects above and beyond a side of the instrument carriage 700. Accordingly, the elongated member opening 760 is disposed at a location not interfacing with the instrument carriage 700. It is worth noting that some implementations have components disposed in a reverse condition, such that the mounting face 751 may include the pogo pins 702 and the instrument carriage may include the printed circuit assembly 752.

In some implementations, the backend mechanism 750 may be mounted to the instrument carriage 700 using a staged engagement and alignment process. This may enable one-handed low force, accurate installation of the backend mechanism onto the instrument carriage 700. In so doing, the input disks may engage the output disks. In some implementations, the order of engagement is dictated by height or length of the mating features and progresses sequentially from less to more constrained and repeatable mating features. In order of engagement, this includes mating of the elongate member 762 followed by the optical fiber connectors, followed by the carriage latch levers entering the slots of the backend mechanism 750. This is followed by the ball mounts entering the V groove kinematic mount seats. For ease of understanding, the reference axes 780a, 780b, and 780c shown in described with reference to FIG. 10 are also identified in FIG. 16 as aligned with the direction of the kinematic mounts 756. In some implementations, the mounts 756 of FIG. 16 may perform the functions of mounts 560 described with reference to FIG. 10. At this time the pogo pins contact the printed circuit assembly contact pads. In the last step, the output disks may rotate to engage slots of the input disks. Finally, the printed circuit assembly in the backend mechanism 750 may communicate fiber calibration info, serial numbers, tool type information, use count information, and encryption data to avoid counterfeiting.

Figure 18:
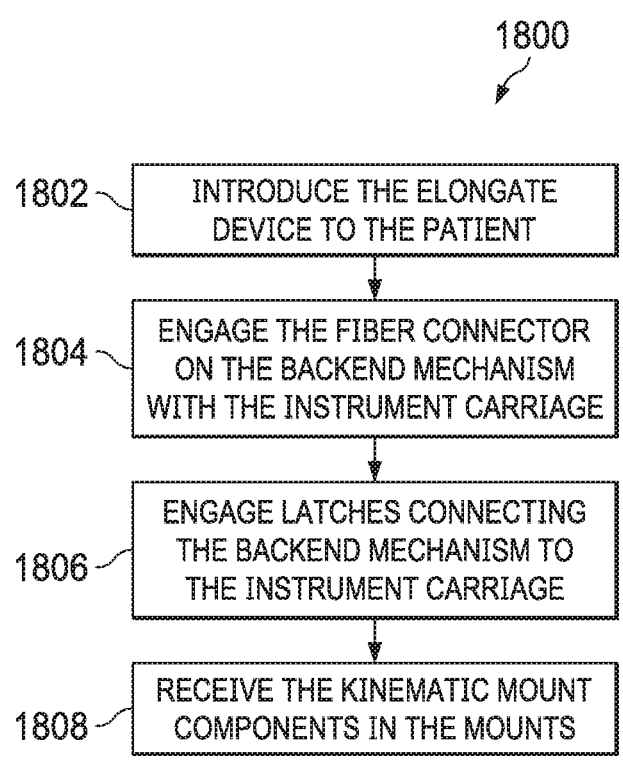
FIG. 18 is a flow chart showing an example method of coupling a backend mechanism of a medical instrument to an insertion assembly according to some implementations.

In some implementations, the backend mechanism 304 may be coupled to the instrument carriage 306 so that the instrument carriage may be advanced toward and away from the patient P (see FIGS. 3A and 3B). FIG. 18 shows a flowchart of an exemplary method 1800 of coupling the backend mechanism 304 to an insertion assembly, such as the instrument carriage 306. It begins at 1802 and includes introducing the elongate member 310 to the patient. As described herein, the elongate device may also include the shape sensor 314. At this stage, only the distal portion of the elongate device may be introduced into the patient.

At 1804, the backend mechanism may engage the instrument carriage 306 by advancing it in the direction of the elongate device, until the fiber connector engages with a corresponding connector on the instrument carriage. In some implementations, the fiber connector may snap into place.

At 1806, the latch interface 496 (FIGS. 4 and 10), which may be disposed at the mounting face and may protrude from the backend mechanism toward the instrument carriage, may be introduced into a receptacle on the instrument carriage. Embodiments including the latch levers 710 may also begin to engage.

At 1808, the mounts 756 receive the kinematic mount components 708. Embodiments of the mounts having V-shaped grooves may enable consistent, repeatable positioning. In some implementations, the kinematic mount components 708 are shaped as hemispherical balls, and the mounts may guide the hemispherical balls of the kinematic mount components into a precise location to achieve sufficient constraint of the backend mechanism in all six degrees of freedom in the manner described herein.

In should be noted that the specific interfacing features of the instrument carriage and backend mechanism may be switched from one to the other without departing from the principles described herein. For example, the instrument carriage may include the kinematic mount components and the backend mechanism may include the mounts.

In some implementations, the latch mechanism enables single-handed installation of the backend mechanism to the motor outputs of the insertion axis carriage while providing high stiffness to counter drive reaction forces and user forces applied to a biopsy needle handle.

In some implementations, latch connectors on the carriage are spring-loaded, and may be squeezed by opposing sides to release the backend mechanism from the instrument carriage. In some implementations, the housing and a clamp on cover over the inputs may prevent fluid ingress during fully submerged cleaning and high-level disinfection processes.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A control system for an elongate member actuated via a pull wire, the system comprising:
   a chassis fixable in place relative to the elongate member during use;
   a pulley carried by the chassis, the pulley having a first pull wire-supporting surface structurally configured to support the pull wire, the pulley being rotatable about a first axis;
   a wall carried by the chassis; and
   a capstan carried by the chassis and rotatable about a second axis aligned at an orthogonal angle relative to the first axis, the capstan having a second pull wire-supporting surface that permits the pull wire to wrap around the capstan, wherein the wall extends circumferentially around the capstan and includes a slit through which the pull wire extends.

2. The control system of claim 1, further comprising an input disk configured to drivably rotate the capstan, wherein the input disk comprises a shaft having a non-cylindrical shape, and wherein the capstan is configured to interface with the non-cylindrical shape in a manner allowing the shaft to rotate the capstan.

3. The control system of claim 1, wherein the capstan comprises a helical groove arranged to wind the pull wire without overlap.

4. The control system of claim 1, comprising a rotation limiter arranged to prevent rotation of the capstan beyond a threshold position.

5. The control system of claim 4, wherein the rotation limiter comprises a mechanical stop arranged to prevent rotation of the capstan beyond the threshold position.

6. The control system of claim 1, further comprising:
a fiber connector extending from the chassis; and
a shape sensor extending from the fiber connector and configured to extend through a length of the elongate member, the shape sensor being arranged to detect a shape of the elongate member,
wherein the fiber connector is configured to communicate information detected by the shape sensor.

7. The control system of claim 1, further comprising an enclosed housing that comprises a service loop adjacent a wall of the enclosed housing, the enclosed housing including an arcing surface sized to accommodate bending of a shape sensor extending between a launch region fixture in the enclosed housing to the elongate member.

8. The control system of claim 7, wherein the service loop is a 180 degree bend in the shape sensor.

9. The control system of claim 8, wherein the enclosed housing comprises a guide defining a guide slot in which the shape sensor extends.

10. The control system of claim 1, wherein the chassis comprises an elongate member opening defining a third axis disposed substantially parallel to the second axis.

11. The control system of claim 10, comprising a coil pipe having a proximal end fixed to the chassis at a connection location, the proximal end of the coil pipe being disposed substantially orthogonal to the third axis defined by the elongate member opening, the pull wire extending through the coil pipe and to the pulley and thereby to the capstan.

12. The control system of claim 1, wherein the chassis comprises a mounting face shaped and configured to interface with an instrument carriage arranged to drive the capstan, the mounting face generally extending along a mounting plane, the mounting face having a first interfacing portion and a second non-interfacing portion arranged side-by-side, the first interfacing portion having a fiber connector and rotational input members, the second non-interfacing portion having an elongate member opening formed such that the elongate member extends from the elongate member opening in a direction substantially orthogonal to the mounting plane.

13. The control system of claim 12, wherein the mounting face comprises one of a plurality of v-shaped grooves and a plurality of locating mounts and the instrument carriage comprises the other of the plurality of v-shaped grooves and the plurality of locating mounts, the plurality of v-shaped grooves being configured to receive the plurality of locating mounts.

14. The control system of claim 1, comprising:
a cover attached to the chassis at an interface to form a cavity therein, the pulley being disposed in the cavity; and
an input disk passing through an opening in the chassis and arranged to rotatably drive the capstan, the input disk having a shielding face to prevent ingress of fluids.

15. The control system of claim 1, comprising:
a fiber connector disposed on and extending from the chassis, the fiber connector being disposed to engage an instrument carriage by translation of the chassis to attach the chassis to the instrument carriage.

16. The control system of claim 1, wherein the wall is spaced from the capstan by a distance less than twice a diameter of the pull wire.

17. The control system of claim 16, wherein the wall is spaced from the capstan by a distance less than the diameter of the pull wire.

18. The control system of claim 1, wherein the wall physically contacts the capstan, the capstan being rotatable relative to the wall.

19. The control system of claim 1, wherein the wall is configured to maintain a light spring contact around substantially a full circumference of the capstan.

20. The control system of claim 1, wherein the wall is constrained to allow the capstan to rotate relative to the wall while maintaining the slit in alignment with the pulley.

* * * * *